(12) United States Patent
Miller

(10) Patent No.: US 9,061,283 B2
(45) Date of Patent: Jun. 23, 2015

(54) SAMPLE METERING DEVICE AND ASSAY DEVICE WITH INTEGRATED SAMPLE DILUTION

(75) Inventor: Cary James Miller, Ottawa (CA)

(73) Assignee: Abbott Point of Care Inc., Princeton, NJ (US)

( * ) Notice: Subject to any disclaimer, the term of this patent is extended or adjusted under 35 U.S.C. 154(b) by 714 days.

(21) Appl. No.: 13/308,943

(22) Filed: Dec. 1, 2011

(65) Prior Publication Data

US 2012/0142020 A1 Jun. 7, 2012

Related U.S. Application Data

(60) Provisional application No. 61/419,489, filed on Dec. 3, 2010.

(51) Int. Cl.
*B01L 3/00* (2006.01)
(52) U.S. Cl.
CPC ............ *B01L 3/52* (2013.01); *Y10T 436/25625* (2015.01); *B01L 2200/16* (2013.01)
(58) Field of Classification Search
CPC ...................................................... B01L 3/52
See application file for complete search history.

(56) References Cited

U.S. PATENT DOCUMENTS

| | | | |
|---|---|---|---|
| 4,945,045 A | 7/1990 | Forrest et al. | |
| 4,946,795 A | 8/1990 | Gibbons et al. | |
| 4,978,610 A | 12/1990 | Forrest et al. | |
| 5,096,669 A | 3/1992 | Lauks et al. | |
| 5,149,630 A | 9/1992 | Forrest et al. | |
| 5,200,051 A | 4/1993 | Cozzette et al. | |
| 5,416,026 A | 5/1995 | Davis | |
| 5,798,215 A | 8/1998 | Cathey et al. | |
| 5,821,399 A | 10/1998 | Zelin | |
| 5,912,134 A * | 6/1999 | Shartle | 435/7.24 |
| 6,750,053 B1 | 6/2004 | Widrig et al. | |
| 7,419,821 B2 | 9/2008 | Davis et al. | |
| 7,682,833 B2 | 3/2010 | Miller et al. | |
| 7,723,099 B2 | 5/2010 | Miller et al. | |
| 2004/0121450 A1 * | 6/2004 | Pugia et al. | 435/287.1 |

(Continued)

FOREIGN PATENT DOCUMENTS

| | | |
|---|---|---|
| CN | 101095040 | 12/2007 |
| EP | 1 977 829 A1 | 10/2008 |

(Continued)

OTHER PUBLICATIONS i-STAT System Manual, Abbott Point of Care, Princeton, NJ (2011) pp. 1-612.

(Continued)

*Primary Examiner* — Melanie Y Brown

(57) ABSTRACT

In one embodiment, the invention is to a sample metering device, comprising a sample holding chamber oriented between a sample entry port and a sample extraction unit, wherein a portion of said extraction unit defines a metered volume of a sample. A diluent may be transported over and/or through the extraction unit to form a diluted sample for sample analysis. In another embodiment, the invention is to an apparatus and method for rapid determination of analytes in liquid samples by various assays including immunoassays incorporating a sample dilution feature, capable of being used in the point-of-care diagnostic field is provided. The devices and methods of the invention preferably are well-suited for high range sample dilution.

19 Claims, 11 Drawing Sheets

(56) References Cited

U.S. PATENT DOCUMENTS

| | | |
|---|---|---|
| 2004/0208794 A1 | 10/2004 | Karg et al. |
| 2005/0009456 A1* | 1/2005 | Sasaki et al. ............... 451/287 |
| 2005/0026302 A1* | 2/2005 | Qian ............................ 436/514 |
| 2008/0281471 A1* | 11/2008 | Smith et al. .................. 700/266 |
| 2010/0009457 A1 | 1/2010 | Cho et al. |
| 2010/0068097 A1 | 3/2010 | Ade et al. |
| 2010/0291666 A1 | 11/2010 | Collier et al. |
| 2010/0297708 A1 | 11/2010 | Collier et al. |
| 2010/0330575 A1 | 12/2010 | Collier et al. |
| 2011/0213229 A1* | 9/2011 | Benoit ......................... 600/345 |
| 2011/0306070 A1 | 12/2011 | Campbell et al. |
| 2012/0142019 A1 | 6/2012 | Miller |
| 2012/0142025 A1 | 6/2012 | Miller |
| 2012/0142026 A1 | 6/2012 | Miller et al. |

FOREIGN PATENT DOCUMENTS

| | | |
|---|---|---|
| EP | 2 145 684 A2 | 1/2010 |
| WO | WO 2005/026689 A2 | 3/2005 |
| WO | WO 2006/071770 A2 | 7/2006 |
| WO | WO 2009/121567 A2 | 10/2009 |

OTHER PUBLICATIONS i-STAT PCA System Manual, Abbott Point of Care, Princeton, NJ (2011) pp. 1-466.
U.S. Appl. No. 61/371,109, filed Aug. 5, 2010, Miller, et al.
U.S. Appl. No. 61/371,085, filed Aug. 5, 2010, Miller, et al.
U.S. Appl. No. 61/371,077, filed Aug. 5, 2010, Campbell, et al.
U.S. Appl. No. 61/371,066, filed Aug. 5, 2010, Miller.
U.S. Appl. No. 61/288,189, filed Dec. 18, 2009, Doyle.
Laurell, et al., Methods in Enzymology, vol. 73, "Electroimmunoassay", Academic Press, New York, 339-340, 346-348, 1981.
M.J. Green (1987) Philos. Trans. R. Soc. Lond. B. Biol. Sci. 316: 135-142.
International Search Report and Written Opinion mailed on May 25, 2012 in corresponding International Application No. PCT/US2011/062843.
Office Action for corresponding Chinese Appl. No. 201180063850.0 dated Jun. 13, 2014.

* cited by examiner

SAMPLE METERING DEVICE AND ASSAY DEVICE WITH INTEGRATED SAMPLE DILUTION

PRIORITY CLAIM

The present application claims priority to U.S. Provisional Application No. 61/419,489, filed Dec. 3, 2010, the entire contents and disclosure of which is hereby incorporated by reference.

FIELD OF THE INVENTION

The present invention generally relates to devices and methods for rapid determination of analytes in liquid samples by various assay techniques including immunoassays incorporating a sample dilution feature, which preferably is suitable for high range sample dilution. The apparatus preferably is capable of being used in the point-of-care diagnostic field, including, for example, use at accident sites, emergency rooms, in surgery, in intensive care units, and also in non-medical environments. The invention is also directed to novel sample metering devices for use in such devices and methods.

BACKGROUND OF THE INVENTION

A multitude of laboratory immunoassay tests for analytes of interest are performed on biological samples for diagnosis, screening, disease staging, forensic analysis, pregnancy testing and drug testing, among others. While a few qualitative tests, such as pregnancy tests, have been reduced to simple kits for a patient's home use, the majority of quantitative tests still require the expertise of trained technicians in a laboratory setting using sophisticated instruments. Laboratory testing increases the cost of analysis and delays the patient's receipt of the results. In many circumstances, this delay can be detrimental to the patient's condition or prognosis, such as for example the analysis of markers indicating myocardial infarction and heart failure. In these and similar critical situations, it is advantageous to perform such analyses at the point-of-care, accurately, inexpensively and with minimal delay.

Many types of immunoassay devices and processes have been described. For example, a disposable sensing device for measuring analytes by means of immunoassay in blood is disclosed by Davis et al. in U.S. Pat. No. 7,419,821, the entirety of which is incorporated herein by reference. This device employs a reading apparatus and a cartridge that fits into the reading apparatus for the purpose of measuring analyte concentrations. A potential problem with such disposable devices is variability of fluid test parameters from cartridge to cartridge due to manufacturing tolerances or machine wear. U.S. Pat. No. 5,821,399 to Zelin, the entirety of which is incorporated herein by reference, discloses methods to overcome this problem using automatic flow compensation controlled by a reading apparatus having conductimetric sensors located within a cartridge.

Electrochemical detection, in which the binding of an analyte directly or indirectly causes a change in the activity of an electroactive species adjacent to an electrode, has also been applied to immunoassays. For an early review of electrochemical immunoassays, see Laurell et al., Methods in Enzymology, vol. 73, "Electroimmunoassay", Academic Press, New York, 339, 340, 346-348 (1981).

In an electrochemical immunosensor, the binding of an analyte to its cognate antibody produces a change in the activity of an electroactive species at an electrode that is poised at a suitable electrochemical potential to cause oxidation or reduction of the electroactive species. There are many arrangements for meeting these conditions. For example, electroactive species may be attached directly to an analyte, or the antibody may be covalently attached to an enzyme that either produces an electroactive species from an electroinactive substrate or destroys an electroactive substrate. See M. J. Green (1987) Philos. Trans. R. Soc. Lond. B. Biol. Sci. 316: 135-142 for a review of electrochemical immunosensors. Magnetic components have been integrated with electrochemical immunoassays. See, for example, U.S. Pat. Nos. 4,945,045; 4,978,610; and 5,149,630, each to Forrest et al. Furthermore, jointly-owned U.S. Pat. No. 7,419,821 to Davis et al. (referenced above) and U.S. Pat. No. 7,682,833 and U.S. Pat. No. 7,723,099 to Miller et al. teach electrochemical immunosensing devices and methods.

Microfabrication techniques (e.g., photolithography and plasma deposition) are attractive for construction of multilayered sensor structures in confined spaces. Methods for microfabrication of electrochemical immunosensors, for example on silicon substrates, are disclosed in U.S. Pat. No. 5,200,051 to Cozette et al., the entirety of which is incorporated herein by reference. These include dispensing methods, methods for attaching biological reagent, e.g., antibodies, to surfaces including photoformed layers and microparticle latexes, and methods for performing electrochemical assays.

In U.S. Pat. No. 4,946,795, Gibbons et al. disclose a sample dilution cartridge that relies on hydrostatic pressure. Jointly-owned U.S. Pat. No. 6,750,053 to Widrig et al., the entirety of which is incorporated herein by reference, teaches sample metering based on a holding chamber with a capillary stop feature.

Notwithstanding the above literature, there remains a need in the art for improved immunosensing devices with a greater range of detection of analytes, including, for example, analytes present at low levels such as cardiac troponin I, and analytes present at high levels, such as CRP. The need also exists for improved devices and methods for metering samples, particularly in point-of-care analyte testing. These and other needs are met by the present invention as will become clear to one of skill in the art to which the invention pertains upon reading the following disclosure.

SUMMARY OF THE INVENTION

The present invention is directed to immunosensing devices and methods of performing an immunoassay with immunosensors incorporating a sample dilution feature preferably suitable for high range dilution, e.g., dilutions that are greater than about 50:1 (v/v diluent:sample), to provide diverse real-time or near real-time analysis of analytes. The invention, in other embodiments, is directed to novel metering devices for metering a biological sample for analysis.

In one embodiment, for example, the invention is to a sample metering device, comprising a sample holding chamber oriented between a sample entry port and a sample extraction unit, wherein a portion of said extraction unit defines a metered volume of a sample. Preferably, a distal portion of said extraction unit defines said metered volume of said sample. The sample may vary widely, and may be selected, for example, from the group consisting of blood, plasma, serum, urine, interstitial fluid and cerebrospinal fluid.

In another embodiment, the invention is to a sensor cartridge for sensing at least one analyte in a sample, comprising: at least one sensor, e.g., an immunosensor, in an analysis conduit; a sample chamber between a sample entry port and a sample extraction unit; a diluent package containing a diluent; a diluent conduit configured for transporting diluent from the diluent package to the sample extraction unit; and a pump configured to transfer said diluent through said diluent conduit, over and/or through said sample extraction unit, and into said analysis conduit. A distal portion of the extraction unit preferably defines a metered volume of the sample. Optionally, the diluent conduit defines a metered volume of diluent. Preferably, the sensor is selected from the group consisting of an immunosensor, an ion sensor, a metabolite sensor, an enzymatic sensor, an enzyme activity sensor and a nucleotide sensor. The cartridge preferably is configured to dilute said sample at a dilution ratio of about 50:1 to about 50,000:1 (v/v diluent:sample).

In another embodiment, the invention is to a method of performing an assay for an analyte in a sample, said method comprising the steps of: introducing a sample into a sample chamber of a cartridge, such as the cartridge described above, wherein the sample chamber terminates in a sample extraction unit; loading said extraction unit with said sample; washing a portion of said sample from the extraction unit using a volume of diluent from a diluent conduit to form a diluted sample; and analyzing said diluted sample for an analyte. The method preferably further comprises the steps of transporting said diluted sample to a sensor, e.g., with a pump; and performing an analyte assay at said sensor. Optionally, the method further comprises a step of characterizing the dilution ratio, e.g., with a dilution determinant marker that may be present in the sample extraction unit, added to the sample before being introduced into the cartridge or otherwise incorporated into the sample during analysis.

In each of these embodiments, the form of the sample extraction also may vary. Preferably, the sample extraction unit comprises a porous hydrophilic material. Examples of materials suitable for the extraction unit include a cellulose material, nitrocellulose, cotton fiber, paper, glass-filled paper, or a transverse filter material. The extraction unit preferably has a porous outer coating. In one aspect, the extraction unit includes a lysing agent, such as sodium deoxycholate or saponin, and the extraction unit may include a dilution determinant marker, preferably suitable for verifying the dilution level of the sample. In one aspect, the extraction unit comprises a reactant such as ferrocene monocarboxylic acid.

The above summary of the present invention is not intended to describe each illustrated embodiment or every implementation of the present invention. The figures and the detailed description that follow more particularly exemplify these embodiments.

BRIEF DESCRIPTION OF THE DRAWINGS

These and other objectives, features and advantages of the present invention are described in the following detailed description of the specific embodiments and are illustrated in the following Figures, in which.

DETAILED DESCRIPTION OF THE INVENTION

The present invention relates to devices, e.g., single-use disposable assay cartridges, and to methods of using such devices to determine the presence or concentration of analytes in a liquid sample. The invention may be particularly adapted for conducting diverse real-time or near real-time assays of analytes. In specific embodiments, the invention relates to devices that are configured for the controlled metered dilution of biological samples (e.g., blood, plasma, serum, urine, interstitial fluid and cerebrospinal fluid) and of analytes in the diluted samples using electrochemical immunosensors or other ligand/ligand receptor-based biosensors.

In a first embodiment, the devices and methods are particularly adapted for low range dilution of a biological sample, e.g., dilutions that are less than about 50:1 (v/v diluent: sample). In this aspect, a sample is metered in a sample dilution chamber to form a metered sample, and the diluent (which may or may not be metered) is added to the metered sample to form a diluted sample that may be subjected to biological analysis, e.g., in an immunoassay on one or more electrodes.

In a second embodiment, the devices and methods are particularly adapted for high range dilution, e.g., dilutions of about 50:1 or greater (v/v diluent:sample), typically from 50:1 to 50,000:1. In this aspect, a portion of the sample is isolated in a fixed sample extraction unit, which preferably is formed of a wicking material. The diluent is subsequently passed over and/or through all or a portion of the fixed sample extraction unit so that it extracts a volumetrically small portion of the sample into the diluent. The resulting highly diluted sample may then be subjected to biological analysis. Those skilled in the art will recognize that the exact dilution ratio at which there is a transition from the first embodiment adapted for low range dilution to the second embodiment adapted for relatively high range dilution may vary depending on parameters including the exact device geometry, fabrication materials and sample type.

I. Sensor Cartridge

A. Low Range Dilution Cartridge Construction

While the present invention is broadly applicable to assay systems, it is best understood in the context of the i-STAT® immunoassay system (Abbott Point of Care Inc., Princeton, N.J., USA), as described in the jointly-owned pending patent applications and issued patents cited herein.

Figure 5:
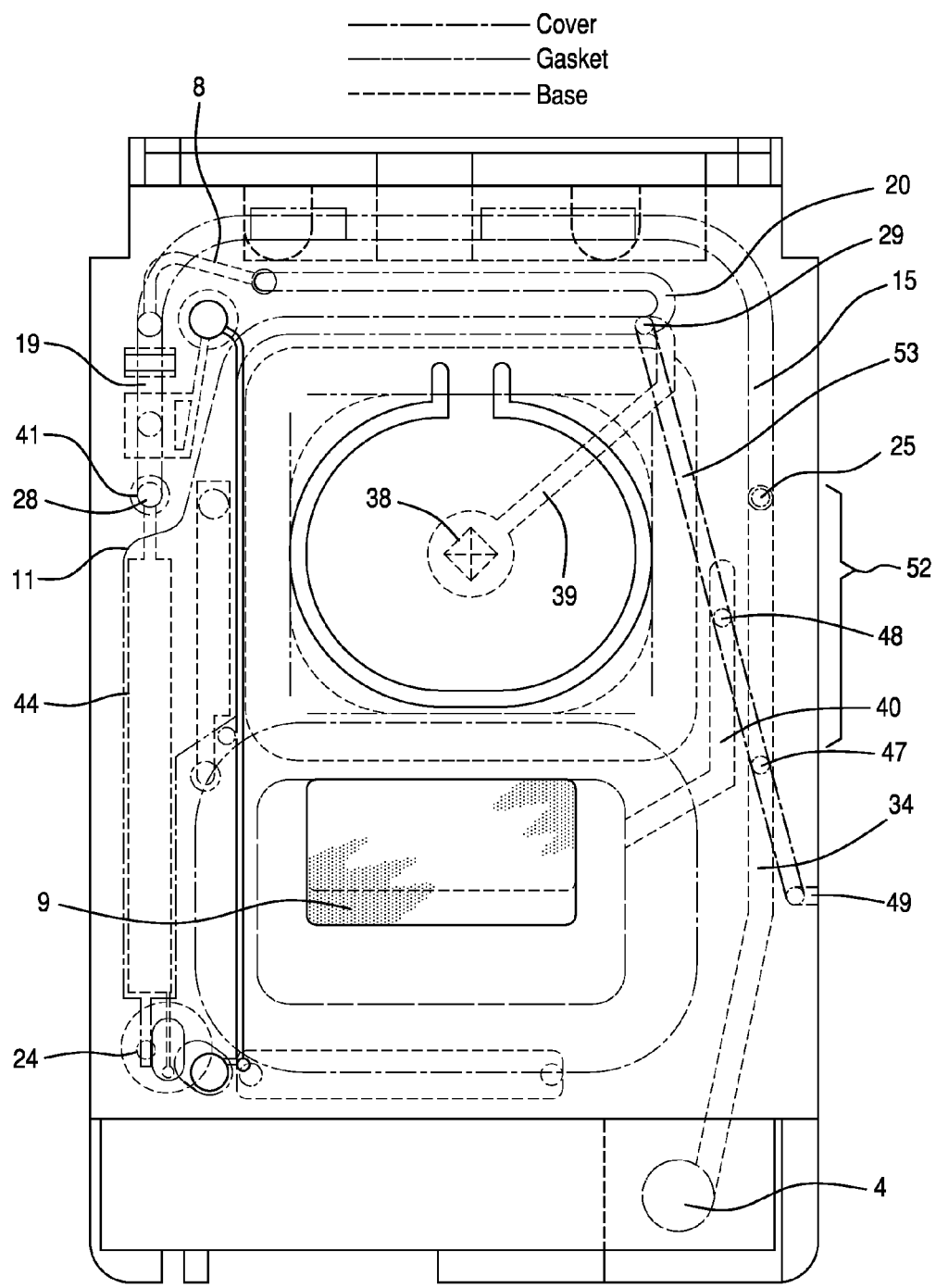
FIG. 5 is a schematic of the layout of an immunosensor cartridge with an integrated sample isolation unit in accordance with one embodiment of the present invention.
Figure 6:
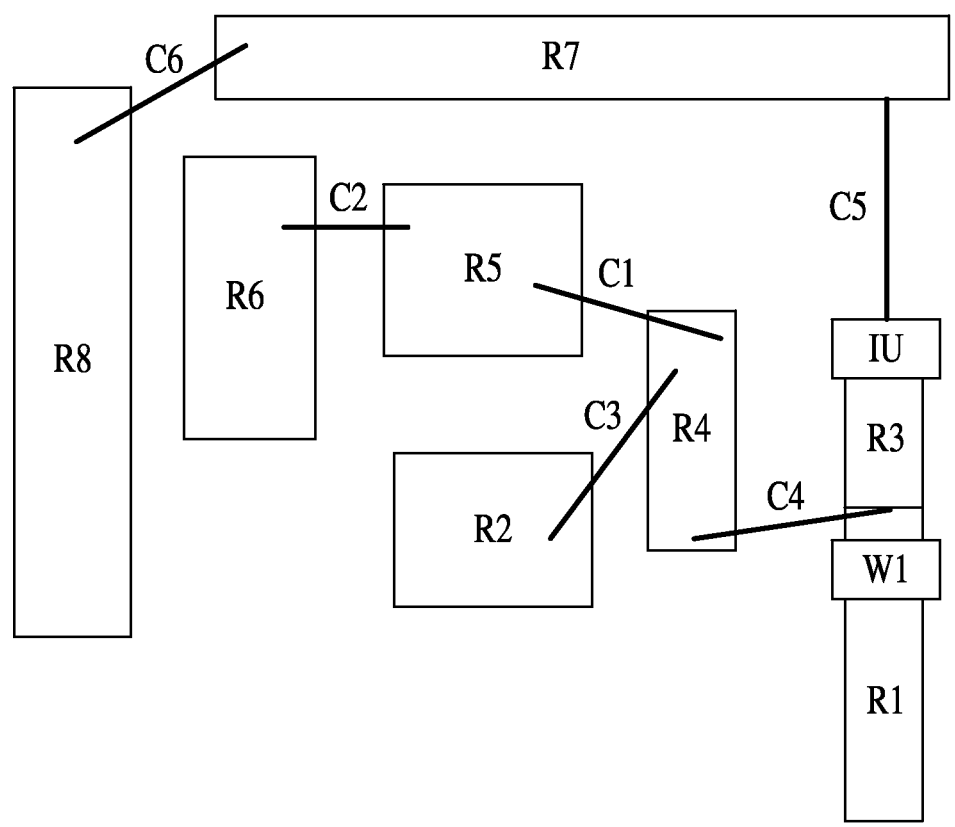
FIG. 6 is a flow chart of the fluid and air paths within an immunosensor cartridge with an integrated sample isolation unit in accordance with one embodiment of the present invention.

The specific form of the devices, e.g., cartridges, of the present invention suitable for sample dilution may vary widely. An exemplary cartridge design according to the first (low range) dilution embodiment of the present invention is shown in FIGS. 1-6 and comprises a cover 1 (FIGS. 1A and 1B), a base 3 (FIG. 3) and a thin-film adhesive gasket 21 (FIG. 2) disposed between the cover 1 and the base 3. The cartridge also includes a flexible, e.g., rubberized, pump membrane 9, shown in FIG. 4, which illustrates an exploded view of the cartridge. FIG. 5 illustrates a composite drawing of the exemplary cartridge superimposing the features of the cover, the base and the gasket. FIG. 6 illustrates a conceptual flow diagram of the fluid and air paths within an immunosensor cartridge with an integrated sample isolation unit suitable for low range sample dilution according to one embodiment of the present invention.

Figure 1A:
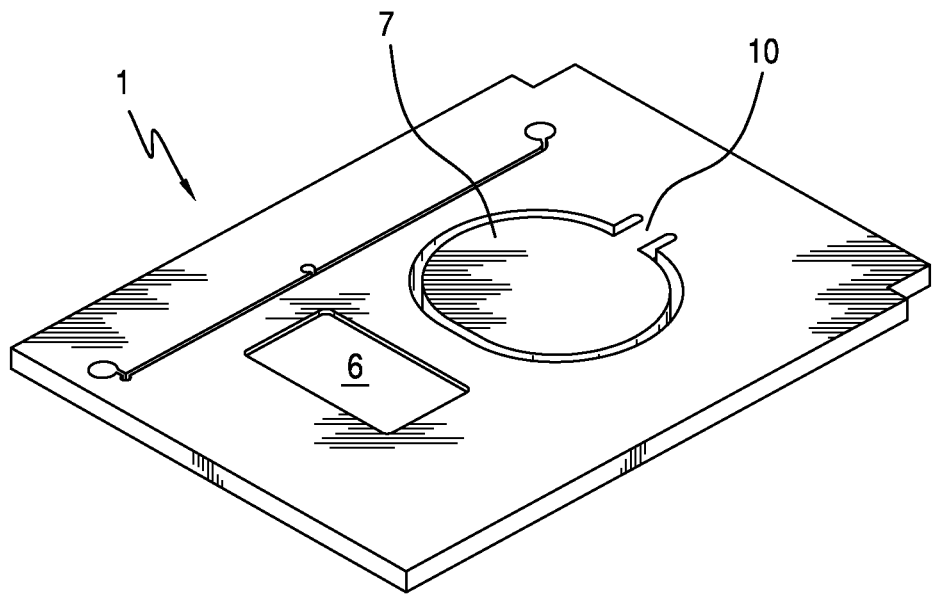
FIGS. 1A and 1B are isometric top and bottom views, respectively, of an immunosensor cartridge cover in accordance with one embodiment of the present invention.
Figure 1B:
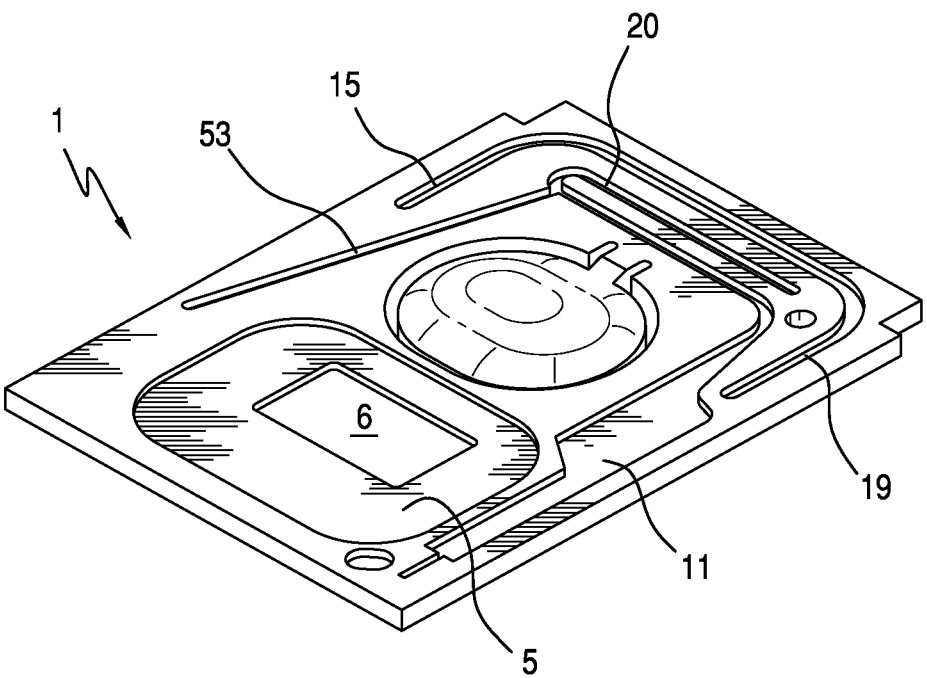

As shown in FIG. 1A, the cover 1 of the cartridge is made of a rigid material, preferably plastic, capable of repetitive deformation without cracking at flexible hinge region 10. The cover 1 further comprises a paddle 7, which is moveable relative to the body of the cover 1, and which is attached to the body by flexible hinge region 10. A pump opening 6 is disposed in the central region of cover 1, and a recessed pump membrane region 5 is provided, preferably on the underside of the cover, as shown in FIG. 1B, for receiving pump membrane 9. Pump membrane 9 may be secured to pump membrane region 5 with an adhesive, which should form an airtight seal in order to allow pump membrane 9 to be repeatably deformed during pumping operations. In other embodiments, not shown, the membrane may be secured to the outer surface of the cover 1. The underside of the cover also preferably includes various conduits and fluid flow features as shown in FIG. 1B and described below.

Figure 2:
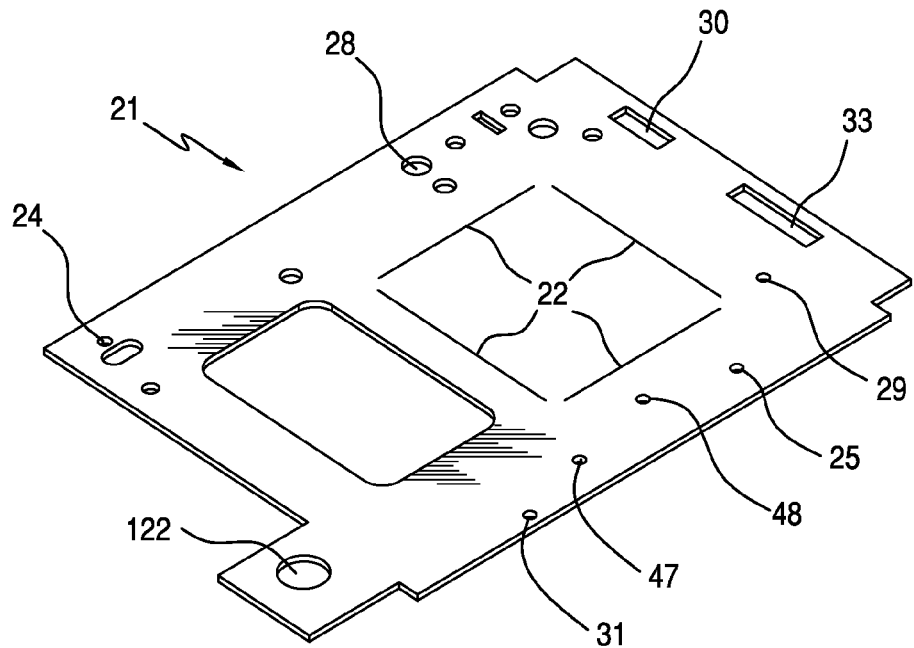
FIG. 2 is a top view of the layout of a tape gasket for an immunosensor cartridge in accordance with one embodiment of the present invention.
Figure 3:
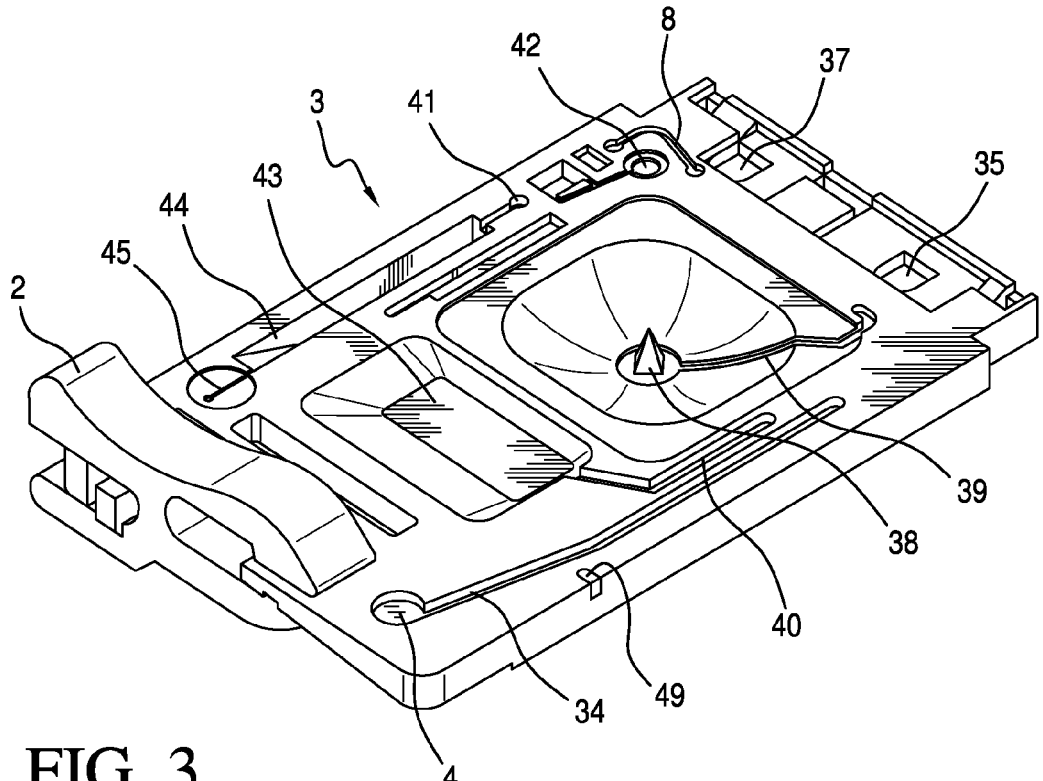
FIG. 3 is an isometric top view of an immunosensor cartridge base in accordance with one embodiment of the present invention.
Figure 4:
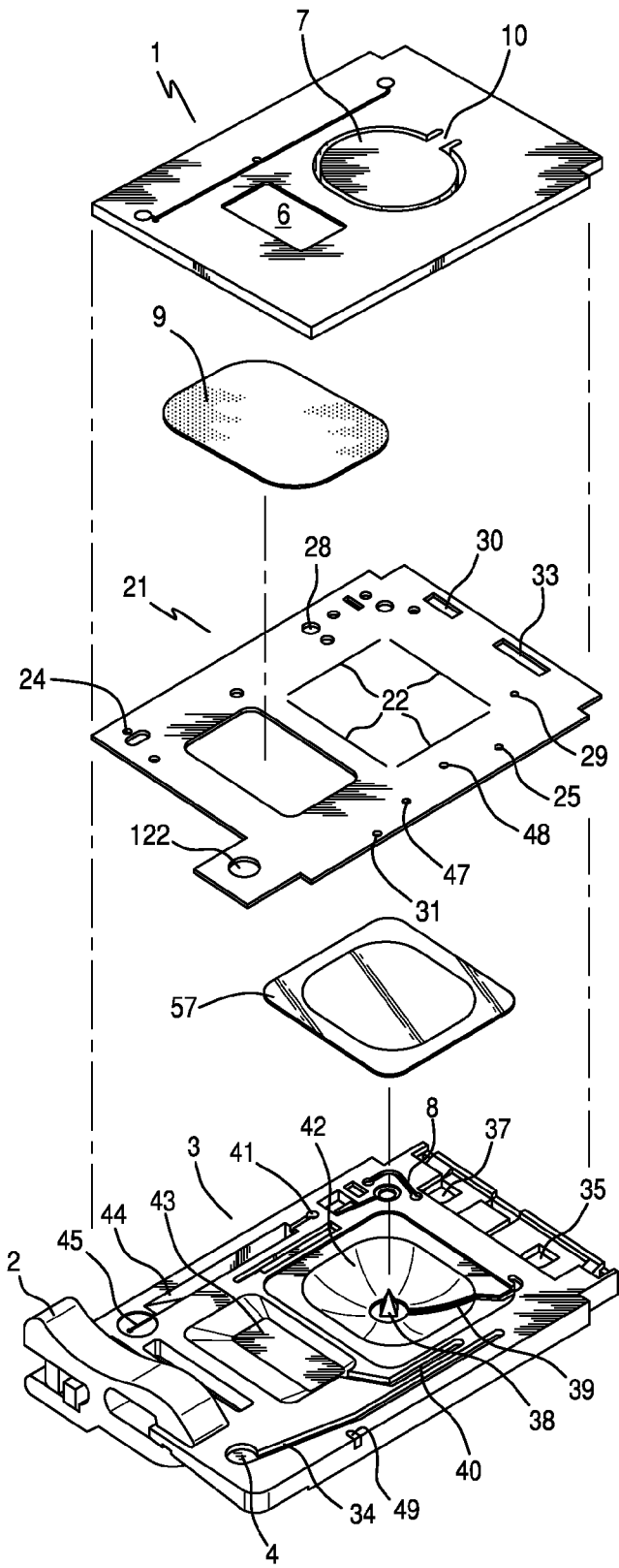
FIG. 4 is an exploded view of an immunosensor cartridge according to one embodiment of the invention.

The base 3, shown in FIG. 3, includes a closure member 2, attached to the main body of the base by prongs at the distal end thereof. One non-limiting embodiment of a closure member is described in jointly-owned U.S. Pat. No. 7,682,833, the entirety of which is incorporated herein by reference. The major features of the base include pump cavity 43, diluent cavity 42, sample entry port 4, and various conduits and fluid flow features as shown in FIG. 3 and described below. The gasket, shown in FIG. 2, is disposed between the cover and base and includes various openings that permit fluids to pass between the conduits in the cover and conduits in the base.

In operation, a biological sample, e.g., whole blood, urine, etc., is introduced into sample entry port 4 and preferably enters sample holding chamber 34 (as shown in FIG. 3) passively via capillary action. The holding chamber 34 extends from the sample entry port 4 to a capillary stop 25. As shown, capillary stop 25 is formed by a hole within the gasket (FIG. 2) that separates holding chamber 34 in the base from analysis conduit 15 in the cover, although in other embodiments, not shown, the capillary stop may be formed by a constriction in a conduit either in the base or the cover of the cartridge. A capillary stop is one example of a sample isolation unit, defined herein as any device capable of isolating the sample in a specific conduit or region of the device. In another embodiment, a sample isolation unit may be formed of a sponge or wicking material that acts to retain the sample.

After introduction of the sample, the closure member 2 can be secured, e.g., slidably secured, over the entrance of sample entry port 4 to prevent sample leakage. The cartridge is then inserted into a reading apparatus in which the sample preferably is automatically manipulated by actuators to detect the analyte in question. The cartridge is therefore preferably adapted for insertion into a reading apparatus, and therefore has a plurality of mechanical and electrical connections adapted for this purpose. It should also be apparent that partial manual operation of the cartridge is possible. When operated upon by a pump means within the reading apparatus, pump membrane 9 exerts a force upon air within an air bladder comprised of cavity 43, which is covered by pump membrane 9, to displace fluids within conduits of the cartridge. When operated by a second pump means, paddle 7 exerts a force upon gasket 21, which can deform because of slits 22 cut therein. (In an alternative embodiment, not shown, a second pump membrane may be substituted for paddle 7.) Gasket 21, in turn, applies pressure on a fluid-containing pouch or package 57, preferably a foil pack comprising a diluent fluid, that is disposed within cavity 42. Thus, upon insertion of the cartridge into the reading apparatus, an actuation mechanism in the reading apparatus applies pressure to the gasket transmitting pressure onto fluid package 57 filled with, for example, about 20 to 200 µL, e.g., about 160 µL of diluent in cavity 42, rupturing fluid package 57 upon spike 38, and expelling diluent into conduit 39, through hole 29 in gasket 21, and into diluent conduit 53 in the cover. Diluent is transported in diluent conduit 53 and is optionally metered in a diluent metering chamber, which is the region within conduit 53 that is between hole 48 (air introduction port) and hole 47 (diluent introduction port). Preferably, holes 48 and 47 are small enough that the surface tension of the diluent contained within the diluent conduit 53 inhibits or prevents the diluent from prematurely passing therethrough. Subsequent pumping action on membrane 9, as described below, allows air to enter the diluent conduit 53 via hole 48, and expels the diluent, preferably a metered amount of diluent, through hole 47 and into sample dilution chamber 52. The diluent then passively mixes with the sample in dilution chamber 52 as the resulting sample/diluent mixture is expelled through capillary stop 25 with continued pumping action and into analysis conduit 15.

In preferred embodiments, the diluent also functions as a wash fluid and may be separately transported to one or more electrodes in the cartridge in order to wash unbound species (e.g., unbound analyte and signal antibodies) from the electrode region after sandwich formation. In the embodiment shown in FIG. 5, diluent conduit 53 is connected to wash conduit 20 in order to effect transport of the diluent, acting as wash fluid, to conduit 20 and ultimately to the electrodes in analysis conduit 15 for washing purposes. As shown, the wash conduit 20 is connected to the analysis conduit 15 via intervening conduit 8 as shown in FIG. 5. The length and orientation of conduits 20, 8 and 15 and dilution chamber 52 preferably are designed such that the diluent mixes with the sample and passes the resulting sample/diluent mixture over the electrodes for sandwich formation prior to directing of the separate diluent stream, acting as wash fluid, to the electrodes to wash unbound species therefrom.

In some embodiments, not shown, the analyzer mechanism applied to the cartridge may be used to inject one or more air segments into the diluent derived from conduit 20 (when the diluent is acting as wash fluid) at controlled positions within the analysis conduit. These segments may be used to help wash the sensor surface and the surrounding conduit using a minimum of fluid. The cover, for example, may further comprise a hole covered by a thin pliable film for this purpose. In operation, pressure exerted upon the film expels one or more air segments into conduit 20 through a small hole 28 in the gasket. See, for example, U.S. Pat. No. 7,723,099, the entirety of which is incorporated herein by reference.

Referring to FIG. 1B, the lower surface of the cartridge cover further comprises a wash conduit 11, an analysis conduit 15 and a diluent conduit 53. Optional coatings within one or more of these conduits may provide hydrophobic surfaces, which may assist in controlling fluid flow between conduits 11, 20 and 15. A recess 40 in the base provides a pathway for air to pass from the pump cavity 43 to hole 48 in the gasket, into conduit 53 in the cover, through hole 47 (diluent introduction port) in the gasket, and into sample dilution chamber 52 (within sample chamber 34) in the base. In operation, diluent contained in conduit 53 in the region between hole 48 and hole 47 (diluent introduction port) in the gasket is pushed through hole 47 and into dilution chamber 52 (a region within sample chamber 34), which contains a metered sample. In this manner, the diluent mixes with the metered sample as the two components are simultaneously pushed through the capillary stop 25 (or other sample isolation unit) and into analysis conduit 15 for sandwich formation and analysis.

As shown in FIG. 2, thin-film gasket 21 comprises various holes and slits to facilitate transfer of fluid between conduits within the base and the cover, and to allow the gasket to deform under pressure where necessary. Hole 122 permits fluid to flow into sample entry port 4 and into sample holding chamber 34. Hole 24 permits fluid to flow from conduit 11 into waste chamber 44. Capillary stop 25 comprises an opening between sample dilution chamber 52 and analysis conduit 15. Hole 28 permits fluid to flow from conduit 19 to waste chamber 44 via optional closeable valve 41. Holes 30 and 33 permit the plurality of electrodes that are housed within cutaways 35 and 37, respectively, to contact fluid within analysis conduit 15. In a specific embodiment, cutaway 37 houses a ground electrode, and/or a counter-reference electrode, and cutaway 35 houses at least one analyte sensor and, optionally, a conductimetric sensor. It should be noted that although the conduits described in connection with the figures variously traverse the gasket, in other embodiments, the conduits may be oriented substantially in the same plane without traversing the gasket, or may traverse the gasket in a manner different than shown in FIGS. 1-5.

Referring to FIG. 3, sample holding chamber 34 extends from the sample entry port 4 to capillary stop 25. Sample dilution chamber 52 (FIG. 5) is disposed within sample chamber 34, specifically between hole 47 and capillary stop 25. As shown, the base includes a vent 49 that facilitates loading of the dilution conduit 53. Specifically, as diluent is allowed to passively enter diluent conduit 53, air that was contained in the diluent conduit is allowed to exit therefrom via hole 31 in the gasket, which is disposed over vent 49. The portion of the sample between hole 47 (diluent introduction port) and the capillary stop 25 (or other sample isolation unit) defines a metered volume of sample for dilution. In exemplary embodiments, the metered sample (prior to dilution) has a volume of from 0.5 µL to 5 µL, e.g., from 0.1 µL to 10 µL or from 0.05 µL to 20 µL.

In accordance with the above description, in one embodiment, the invention is directed to a sample metering device, comprising a sample holding chamber oriented between a sample entry port and a sample isolation unit and having a diluent introduction port disposed therebetween for introduction of a diluent into the sample holding chamber. In this embodiment, the volume within the sample holding chamber between the diluent introduction port and the sample isolation unit defines a metered volume of a sample for analysis.

In other embodiments of the invention, not shown, multiple fluid-containing packages are utilized. In some such embodiments, each fluid-containing package contains a different fluid, e.g., diluent, a wash fluid, and/or one or more reagent fluids. An air sac or bladder is comprised of recess 43, which is sealed on its upper surface by pump membrane 9. The air bladder is one embodiment of a pump means, and is actuated by pressure applied to membrane 9, which displaces air in conduit 40 and thereby displaces the diluent from diluent conduit 53 (optionally metered in a diluent metering chamber) and into sample dilution chamber 52, where sample dilution occurs, and ultimately displacing the diluted sample through capillary stop 25 and into analysis conduit 15. Other types of pumps suitable for use in the present invention include, but are not limited to a flexible diaphragm, a piston and cylinder, an electrodynamic pump, and a sonic pump.

The region between which diluent enters the sample dilution chamber (e.g., gasket hole 47) from conduit 53 and the capillary stop 25 together define a predetermined or metered volume of the sample dilution chamber. An amount of the sample corresponding to this volume together with diluent from diluent conduit 53 are displaced into the analysis conduit 15 when the air bladder or pump is depressed. This arrangement is, therefore, one embodiment of a metering means for delivering a metered amount of an originally unmetered sample into the conduits of the cartridge.

Metering may be advantageous, for example, if quantitation of the analyte is required. In other embodiments, for example when determining the mere presence of an analyte, metering is not necessary. A waste chamber 44 is provided for sample and/or fluid that is expelled from the conduit to prevent contamination of the outside surfaces of the cartridge. A vent 45 connecting the waste chamber 44 to the external atmosphere is also provided to facilitate fluid entry into waste chamber 44. A feature of the cartridge of one embodiment of the present invention is that once a sample is loaded, analysis can be completed and the cartridge discarded without the operator or others contacting the sample.

In some embodiments of the invention, a closeable valve is provided between the analysis conduit and the waste chamber. See, for example, the materials described in jointly-owned U.S. Pat. No. 7,419,821, which is referenced above and hereby incorporated by reference in its entirety. In one embodiment, the valve is comprised of a dried sponge material that is coated with an impermeable substance. In operation, contacting the sponge material with the sample or another fluid results in swelling of the sponge to fill cavity, thereby substantially blocking further flow of liquid into the waste chamber. The wetted valve also blocks the flow of air between the analysis conduit and the waste chamber, which permits the first pump means connected to the sample dilution chamber to displace fluid within the wash conduit, and to displace fluid from the wash conduit into the analysis conduit in the following manner. After the sample is exposed to the sensor for a controlled time, the sample is moved into the post-analytical conduit where it can be amended with a reagent. The sample can then be moved back to the sensor and a second reaction period can be initiated. Alternatively, the post-analysis conduit can serve simply to separate the sample segment from the sensor. Within this post-analysis conduit is a single closeable valve, which connects the air vent of the analysis conduit to the diaphragm air pump. When this valve closes, the sample is locked in the post analytical conduit and cannot be moved back to the sensor chip. There are several different design examples for this valve that are encompassed within the present invention. Some designs are activated mechanically, while others activate upon contact with a liquid. Other types of closeable valves that are encompassed by the present invention include, but are not limited to, a flexible flap held in an open position by a soluble glue or a gelling polymer that dissolves or swells upon contact with a fluid or sample thus causing the flap to close, and alternatively, in one specific embodiment, a thin layer of a porous paper or similar material interposed between a conduit and either the waste chamber or ambient air such that the paper is permeable to air while dry, but impermeable when wet. In the latter case, it is not necessary that the closeable valve be interposed between a conduit and the waste chamber, as the valve passes little to no liquid before closing. Rather, the valve is appropriately placed when positioned between a conduit and the ambient air surrounding the cartridge. In practical construction, a piece of filter paper is placed on an opening in the tape gasket in the fluid path to be controlled. Air can readily move through this media to allow fluid to be moved through the fluid path. When the fluid is pushed over this filter, the filter media becomes filled with liquid and further motion through the fluid path is stopped. As the filter becomes filled, increasing pressure is required to move liquid through the pores of the filter. Air flow through the filter is also minimized or prevented. This valve embodiment requires very little liquid to actuate the valve, and actuation occurs rapidly and reliably. Valve materials, dimensions, porosity, wettability, swelling characteristics and related parameters are selected to provide for rapid closure, within one second or more slowly, e.g., up to 60 seconds, after first contact of the valve with the sample. In certain embodiments of the invention, the closeable valve is a mechanical valve. In one embodiment, a latex diaphragm is placed in the bottom of the air bladder on top of a specially-constructed well. The well contains two openings that fluidically connect the air vent to the sample conduit. As the analyzer plunger pushes to the bottom of the air bladder, it presses on the latex diaphragm, which is adhesive-backed, and seals the connection between the two holes. This blocks the sample air vent and locks the sample in place.

FIG. 6 is a schematic view of the fluidics within an immunosensor cartridge in accordance with one embodiment of the present invention. Regions R1-R8 represent specific immunosensor cartridge components and C1-C6 represent the fluidic connections between the components. W1 represents a vent, e.g., a wicking vent, which facilitates fluid movement of diluent from R4 to R3. In particular, R1 is the sample entry port and associated components for transporting the sample to W1; R2 is the pump (e.g., air bladder) used to displace the diluent from the diluent conduit (optionally diluent metering chamber) to a metered volume of sample for dilution; R3 represents the sample dilution chamber, which terminates in a sample isolation unit IU (e.g., capillary stop); R4 is the diluent conduit (optionally comprising a diluent metering chamber); R5 represents a diluent package and may include a diluent metering chamber; and R6 represents an optional reagent package. R6 represents an optional holding chamber for a reagent or wash fluid, which may, for example, pass to conduit 20. The conduit 20, in certain embodiments, can be coated with a reagent which dissolves into the fluid released from R5 and/or R6. The reagent amends the fluid so that it can better serve as a wash/analysis fluid in embodiments where the presence of this reagent in the dilution fluid in R4 would not be ideal for the assay. In an alternative embodiment of the invention, C2 can optionally directly link R4 with R6, such as, for example via a T junction. R7 represents the analysis conduit and corresponding electrodes; and R8 is a waste chamber.

Figure 7:
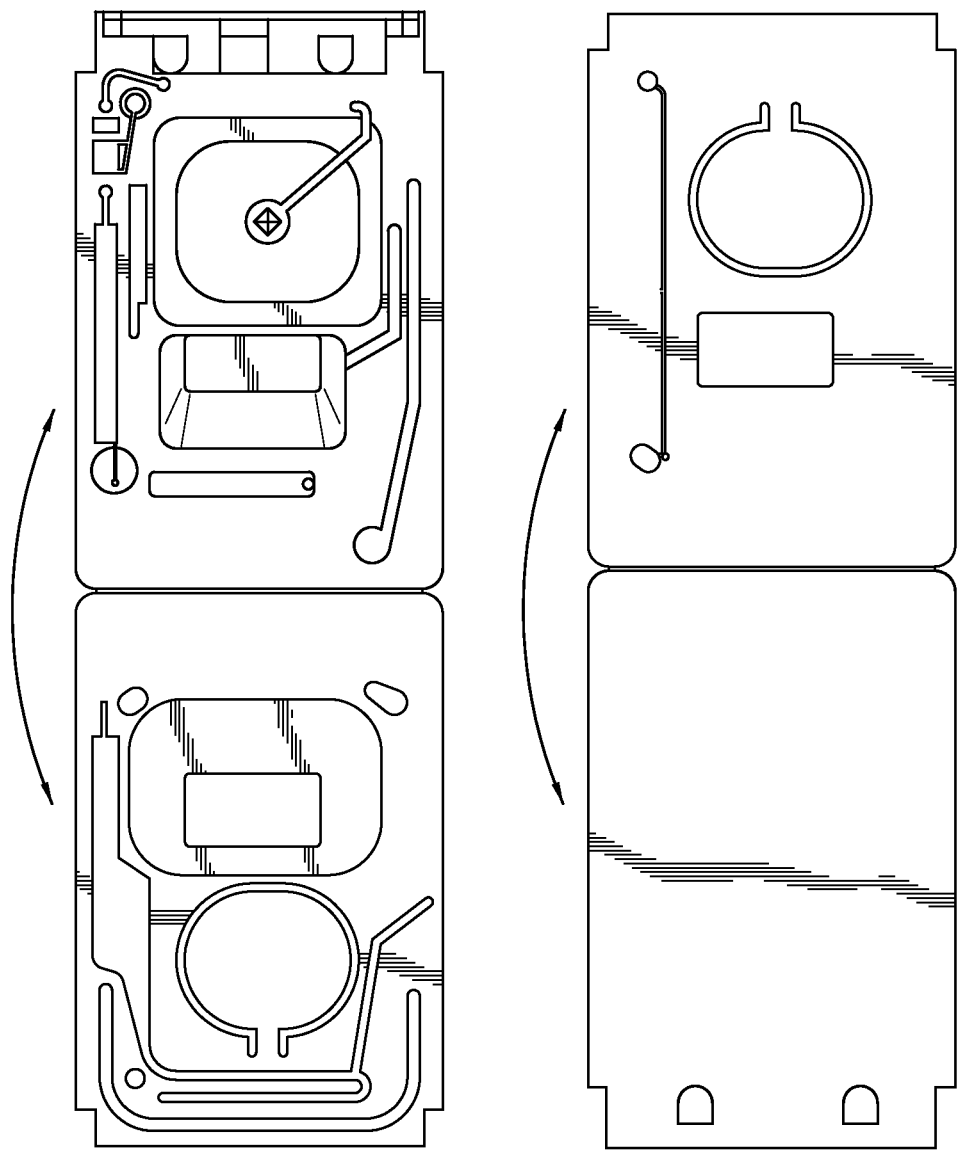
FIG. 7 illustrates a foldable cartridge housing in accordance with one embodiment of the present invention.

As shown in FIG. 7, in some embodiments of the present invention, the immunosensor cartridge is adapted to a foldable cartridge design of the type described in jointly-owned U.S. Pat. Appln. No. 61/288,189, entitled "Foldable Cartridge Housings for Sample Analysis," filed Dec. 18, 2009, the entirety of which are incorporated herein by reference.

Although the use of capillary stops in a sample metering chamber are known, the use of a sample isolation unit that comprises a porous material (e.g., a porous hydrophilic or hydrophobic material, a cellulose material, nitrocellulose, cotton fiber, paper, glass-filled paper, a wicking material, a matrix material or other porous material) to form a metered sample is heretofore unknown.

Thus, in one embodiment, the invention is to a sample metering device, comprising a housing comprising a sample chamber located between a sample entry port and a sample isolation unit, wherein the volume between the entry port and the sample isolation unit defines a metered volume of a sample for analysis, and wherein the sample isolation unit comprises a porous material. Although metered samples thus formed may be used in the dilution embodiments of the invention, the use of sample isolation units that comprise a porous material is not limited to the dilution embodiments discussed herein and may be adopted in immunoassay devices and methods that do not form diluted samples.

B. High Range Dilution Cartridge Construction

Figure 8:
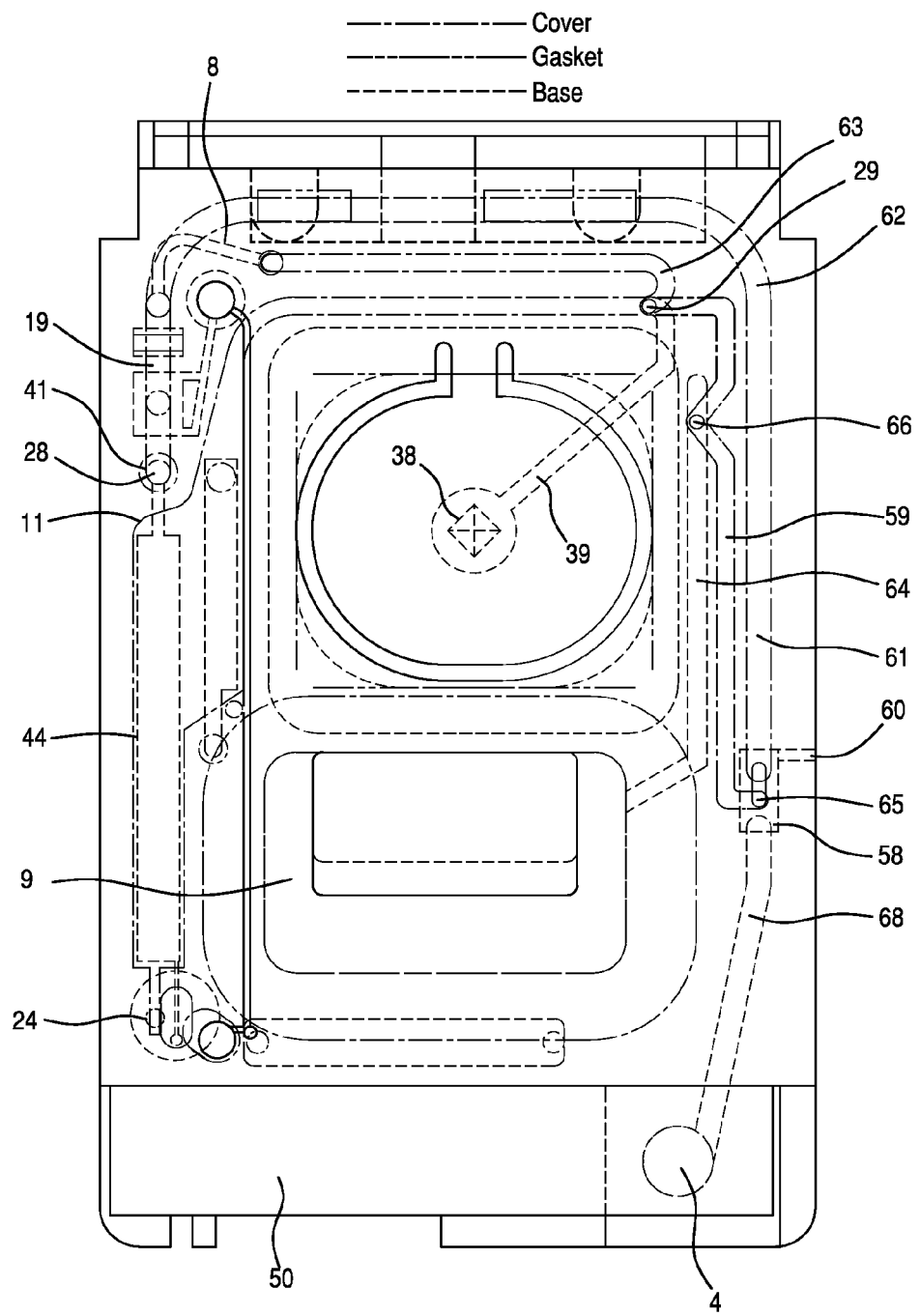
FIG. 8 is a schematic of the layout of an immunosensor cartridge with an integrated fixed sample extraction unit in accordance with one embodiment of the present invention.
Figure 9:
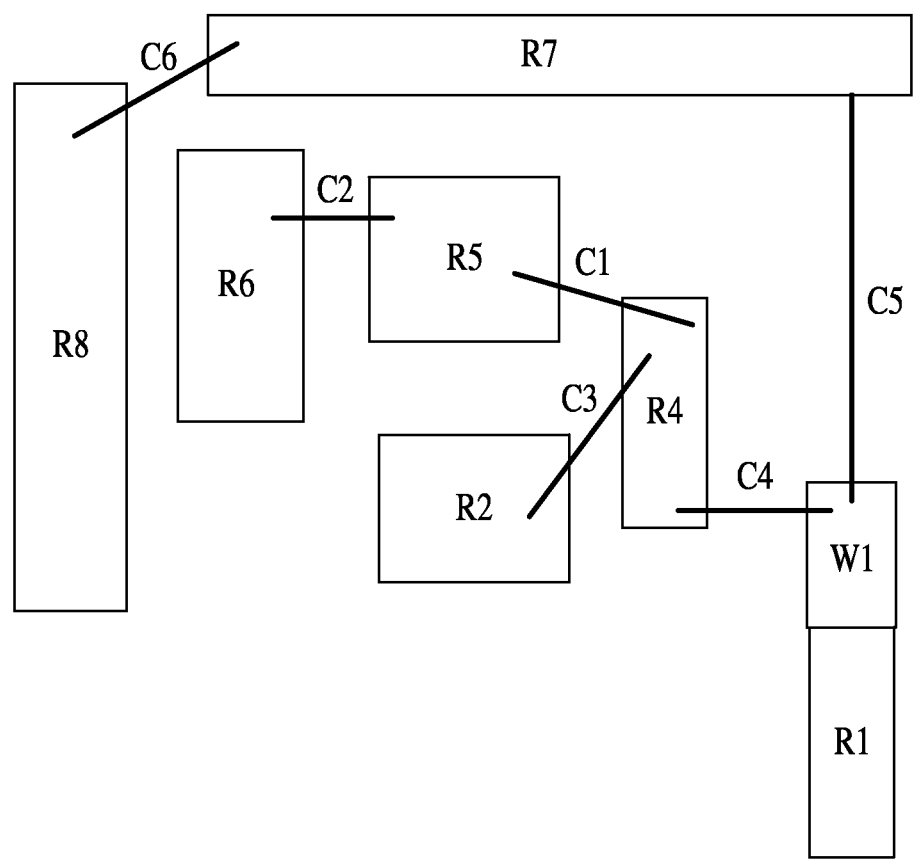
FIG. 9 is a flow chart of the fluid and air paths within an immunosensor cartridge with an integrated fixed sample extraction unit in accordance with one embodiment of the present invention.

In the second dilution embodiment of the invention, a sample is diluted at a high dilution ratio, e.g., greater than about 50:1. The specific form of devices, e.g., cartridges, according to this embodiment of the invention may vary widely. An exemplary cartridge design according to the second dilution embodiment (high range dilution) of the present invention is shown in FIGS. 8 and 9. FIG. 8 illustrates a composite drawing of an exemplary cartridge superimposing the features of the cover, the base and the gasket according to one embodiment of the invention, and FIG. 9 provides a flow diagram of the fluid and air paths within an immunosensor cartridge with an integrated fixed sample extraction unit in accordance with one embodiment of the present invention. In various embodiments, dilutions in the range of about 50:1 to about 50,000:1, e.g., from 100:1 to 1,000:1 or from 5,000:1 to 25,000:1, can be performed.

In many respects, the devices and methods for the high range dilution embodiments are similar to the low range dilution embodiments. The primary differences will be highlighted herein, but otherwise the cartridges preferably are substantially as described above in connection with the low range dilution embodiments. For example, in the high range dilution embodiments, a much smaller amount of sample is metered than in the low range dilution embodiments. In addition, the metering itself is performed in a different manner. In the high range dilution embodiments, the metering is conducted at the fixed sample extraction unit, preferably the distal end thereof, instead of a metered sample that is formed between two openings (47 & 25 of FIG. 5) that define the sample dilution chamber (52). Further, in the high range dilution embodiments, diluent passes over and/or through all or a portion of the fixed sample extraction unit causing the sample contained therein to be extracted into the diluent and thereby forming a highly diluted sample.

As a specific example, high range dilution may be conducted using a "wick wash" or fixed extraction process design. In this embodiment of the present invention, sample is introduced into the device and is allowed to flow, e.g., passively flow through capillary action, until it reaches a fixed sample extraction unit. After contacting the fluid sample, the extraction unit preferably becomes saturated with the sample and inhibits or prevents further flow of the sample. A distal portion of the extraction unit preferably defines a metered volume of a sample for dilution. In this embodiment, a very small reproducible amount of sample (e.g., 100 pL to 2 µL, from 2 nL to 1 µL or from 50 nL to 0.5 µL) is extracted from the fixed sample extraction unit in order to form a diluted sample.

As shown in FIG. 8, the immunosensor cartridge includes a sample entry port 4, a sample introduction chamber 68 and a fixed sample extraction unit 58. At the distal end of the extraction unit 58 is a sample dilution chamber 61 where formation of the diluted sample primarily occurs. As shown, the sample introduction chamber 68 is oriented in the base and the sample dilution chamber is positioned in the cover of the cartridge, although in other embodiments both chambers may be oriented in the cover or in the base. The dilution chamber 61 preferably is oriented proximate, i.e., adjacent, the fixed sample extraction unit 58 such that as sample is extracted from the fixed sample extraction unit 58 by diluent, it passes to the sample dilution chamber for passive mixing 61. As shown, the fixed sample extraction unit 58 is oriented in the base. In other embodiments, not shown, the fixed sample extraction unit 58 is oriented in the cover or in both the base and the cover (extending therebetween). Sample extraction unit 58 is loaded with sample and defines a metered volume of sample for dilution. A vent 60 (e.g., vent wick) may be provided adjacent the fixed sample extraction unit 58 to facilitate gas removal as the extraction unit 58 is loaded with sample.

An analysis conduit 62 (substantially similar to the analysis conduit 15 in the low range dilution embodiment) comprising an analyte-responsive surface and positioned in the cover of the cartridge is fluidly connected to sample dilution chamber 61. The immunosensor cartridge further includes a wash conduit 63 for retaining diluent used to wash or treat the sensor after sandwich formation. The wash conduit 63 is connected to the analysis conduit 62 via intervening conduit 8 in the base as shown in FIG. 8. A diluent conduit 59 is connected to the wash conduit 63. Diluent is released from fluid package 57 upon rupturing of the package on spike 38. The released diluent is then transferred via conduit 39, through hole 29 in the gasket, and into diluent conduit 59. In some embodiments, not shown, the fluid package includes multiple individual fluid packages (e.g., rupturable foil pouches). In this aspect, each individual fluid package may contain a different fluid composition, while in other embodiments, one or more of the multiple pouches may contain the same fluid composition. Each package may have its own associated pumping mechanism or may share a pumping mechanisms.

In operation, after the sample has saturated the fixed sample extraction unit 58, the diluent package 57 is ruptured allowing diluent to flow into diluent conduit 59 as discussed above. The diluent flows in diluent conduit 59 until it reaches membrane opening 65 (diluent introduction port), which optionally comprises a capillary stop. At this point, pump membrane 9 is actuated causing air to be delivered through conduit 64 and into diluent conduit 59 via hole 66. The air entering the diluent conduit causes diluent contained in diluent conduit 59, specifically between hole 66 and opening 65 (e.g., a metered diluent), to pass through opening 65 (diluent introduction port) and into contact with fixed sample extraction unit 58. Upon contact with the extraction unit 58, the diluent acts to extract a small volume of sample therefrom, and the resulting diluted sample, preferably a highly-diluted sample, is allowed to pass into sample dilution chamber 61. The diluted sample then passes to analysis conduit 62. As will be appreciated, the desired dilution ratio may be obtained by controlling where the dilution conduit contacts the fixed sample extraction unit and by controlling the volume of the diluent, e.g., metered diluent in the diluent chamber. Preferably, the portion that is washed or extracted from fixed sample extraction unit 58 is particularly small, e.g., less than 2 vol. %, less than 0.2 vol. %, or less than 0.01 vol. %, of the total sample contained in the fixed sample extraction unit 58 prior to contact with the diluent.

In addition to diluting the sample, the diluent preferably functions as a wash fluid as in the low range dilution embodiment discussed above. In these embodiments, upon rupture of diluent package 57, some diluent is allowed to flow through hole 29 and into wash conduit 63 (wash conduit 63 is shown in fluid communication with diluent conduit 59). Wash conduit 63 is in fluid communication with analysis conduit 62 via intervening conduit 8, in order to allow the diluent, acting as a wash fluid, to wash any unbound components from the region of the electrodes.

In certain embodiments of the present invention, the invention is to a fixed sample extraction process for high-range dilutions comprising: loading a fixed sample extraction unit with a sample, wherein the fixed sample extraction unit is proximate to a sample dilution chamber; washing (e.g., extracting) a portion of the sample from the extraction unit using a diluent, preferably a metered volume of diluent, from a diluent conduit to form a diluted sample; transporting the diluted sample to a sensor; and performing an analyte assay at the sensor.

In another embodiment, the fixed sample extraction process further comprises adding a dilution determinant marker to the sample; measuring the dilution determinant marker concentration in the sample prior to introducing said sample into the sample dilution chamber; measuring the dilution determinant marker concentration in a portion of the sample washed from the extraction unit; comparing the dilution determinant marker concentration in the sample prior to introducing said sample into the sample dilution chamber with the dilution determinant marker concentration in the portion of the sample washed from the extraction unit; and calculating the dilution ratio. In still other embodiments, the fixed sample extraction process includes a step of adding a dilution determinant marker to the extraction unit; measuring the dilution determinant marker concentration in a portion of the sample washed from the extraction unit; and calculating the dilution ratio.

FIG. 9 is a schematic view of the fluidics within an immunosensor cartridge with an integrated fixed sample extraction unit in accordance with one embodiment of the present invention. Regions R1, R2 and R4-R8 represent specific immunosensor cartridge components, C1-C6 represent the fluidic connections between the components and W1 represents the controlled dilution device for high-range dilutions (e.g., a fixed sample extraction unit). In particular, R1 is the sample introduction chamber; R2 is the pump (e.g., air bladder) used to displace the diluent from the diluent conduit R4 (e.g., diluent metering chamber) to a metered volume of sample for dilution; R5 is the diluent package; R6 represents an optional reagent package; R7 comprises the analysis conduit; and R8 is a waste chamber. In an alternative embodiment, C2 can optionally directly link R6 with R4, such as, for example via a T junction.

C. Composition of the Sample Isolation Unit and Fixed Sample Extraction Unit

In accordance with certain aspects of the present invention, the materials that form the fixed sample extraction unit or the sample isolation unit in the low range dilution embodiments preferably are selected to serve as an effective fluid transport mechanism. Exemplary materials include any material that may be suitably configured to exhibit acceptable transport kinetics. To ensure reliable extraction of analyte from the sample isolation unit or fixed sample extraction unit, hydrophilic materials or coatings are preferably employed. In some embodiments, the entire matrix is comprised of a hydrophilic material, while in other embodiments, only the conduit contact edge and the conduit walls are so comprised. Exemplary materials for the fixed sample extraction unit or sample isolation unit include cellulose, nitrocellulose, cotton fiber, paper and glass-filled paper (e.g., Leukosorb®, Pall Corporation, Port Washington, N.Y., USA). In other embodiments of the invention, this area of the immunosensing device may be corona treated during assembly to promote hydrophilicity. Use of a hydrophilic material ensures that bubbles formed in the diluent are not trapped on the sample isolation unit or fixed sample extraction unit, thereby impeding analyte transfer. In some embodiments, particularly in the low range dilution embodiments, as discussed above, the sample isolation unit may comprise a capillary stop and may not comprise porous or matrix-type material.

In embodiments of the invention directed to high-range dilutions, suitable materials may be less porous (e.g., having a porosity of from 20 μm to 0.1 μm, e.g., from 10 μm to 0.2 μm or from 5 μm to 0.5 μm, as determined by microscopy (e.g., visible or scanning electron microscopy)), than those materials suitable for relatively smaller dilutions, the effect of which is that the sample takes longer to move through the matrix of the fixed sample extraction unit to the extraction face. In addition, in some embodiments of the invention, materials generally considered as transverse filter materials (e.g., 0.2 μm water purification filters with a porous outer coating, porous glasses such as Vycor®, (Corning Incorporated, Corning, N.Y., USA), treated lateral flow materials from American Filtrona Co. (Richmond, Va., USA), filter media from Millipore Corporation (Billerica, Mass., USA), filter media from Whatman® Schleicher & Schuell® (Maidstone, Kent, UK, and others) may be used in a lateral mode as the extraction unit material. In these high dilution embodiments, a small pore volume relative to a comparatively large volume of diluent is advantageous (e.g., extraction unit dimensions (length, width, height) of 2 mm×2 mm×100 μL versus 100 μL of diluent) for controlled dilution. In this aspect, only a sample within a few hundred microns or less is extracted from the edge of the filter into the diluent as the diluent is washed over the fixed sample extraction unit. Exemplary volumes of sample that are incorporated into the diluted sample may range from 50 nL to 0.5 μL, from 2 nL to 1 μL or from 100 pL to 2 μL.

Figure 10A:
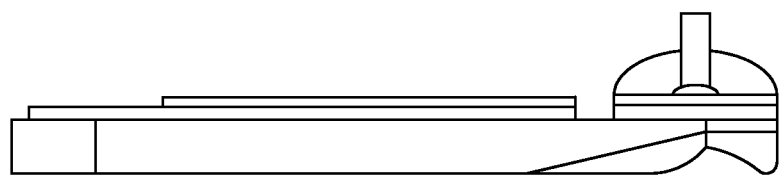
FIG. 10A shows a side view of one embodiment of the immunosensor cartridge of the present invention.
Figure 10B:
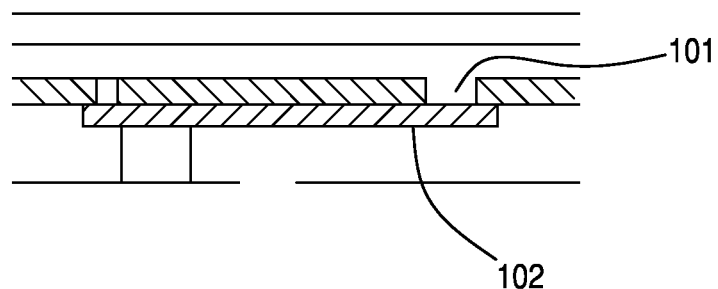
FIG. 10B shows enlarged details of the hemolysis detection device therein.

The porosity of the isolation unit or extraction unit may be selected to preferentially trap or retard the movement of white and red blood cells. See, for example, the materials described in jointly-owned U.S. Pat. No. 5,416,026, which is hereby incorporated by reference in its entirety. As such, in certain embodiments, the sample that is diluted in the dilution step may be a plasma fraction rather than whole blood. In such embodiments, the isolation unit or extraction unit is formatted as a lateral flow element where blood enters on one side and plasma predominates towards the other side. This configuration is shown in FIGS. 10A and 10B. In the device of FIG. 10B, a hemolysis detection device sample orifice 101 for contacting the whole blood sample with dry separation material 102 is located proximate to the blood entry port 4 (FIG. 8). The plasma or serum fraction wicks along dry separation material 102, thus becoming separated from whole blood cells. In other embodiments, the isolation unit or extraction unit also includes a lysing agent that lyses only the red blood cells in the sample, or both the red and the white blood cells. Suitable lysing agents may, in some embodiments, be dry coated onto the isolation unit or extraction unit for dissolution into the sample. Preferred lysing agents include sodium deoxycholate and saponin.

D. Dilution Verification

In accordance with various embodiments of the present invention, the effective dilution ratio and reproducibility of any given cartridge design can be ascertained or confirmed by adding one or more dilution determinant markers to the sample prior to introduction to the immunosensing device. In some embodiments, a measurable concentration of ferricyanide, e.g., from 0.01 to 50, from 0.1 to 10 or from 1 to 5 mM ferricyanide, is added to the sample. Other electrochemical species suitable for use as the dilution determinant marker include ruthenium hexamine and a ferrocene, e.g., ferrocene monocarboxylic acid. In some exemplary embodiments, the dilution determinant marker is selected from the group consisting of an electrochemical species, ferricyanide, ruthenium hexamine, a ferrocene, ferrocene monocarboxylic acid, an optional dye, fluorescein, an acridinium salt, methylene blue and the like. Alternative ways of verifying sample dilution include the use of an optical dye dilution determinant marker (e.g., fluorescein, an acridinium salt, and methylene blue). In these embodiments, a spectrophotometer may be used to determine the ratio of concentrations and hence, the dilution factor. In still other embodiments, dilution can be confirmed using a sodium ion concentration dilution, e.g., with an integrated sodium ion sensor with the initial sample sodium concentration verified in a second cartridge.

In one embodiment, the invention is to a method of performing an assay for an analyte in a fluid sample with a cartridge having an integrated sample dilution element, where the cartridge is adapted for insertion into a reading apparatus, the method comprising: (a) introducing a fluid sample into a sample holding chamber of a cartridge with a sample dilution element, wherein at least a portion of said dilution element determines a volume of sample for dilution, and wherein said dilution element further comprises a predetermined known amount of a dilution determinant marker capable of dissolving into said sample; (b) pumping a metered volume of diluent from a diluent chamber in said cartridge, to said sample dilution element to form a diluted sample; (c) pumping the diluted sample to a sensor in a sensing region of said cartridge; (d) measuring the concentration of said dilution determinant marker in said diluted sample; and (e) determining the dilution ratio of the diluted sample from said measured concentration in step (d) and said predetermined known amount of step (a). The diluted sample may be at a dilution ratio of from about 1:1 to 50:1 parts by volume diluent:sample, or from 50:1 to about 50,000:1 parts by volume diluent:sample. The dilution ratio value determined in step (e) preferably is used to calculate the concentration of the analyte in the undiluted sample.

The predetermined known amount of dilution determinant marker may, for example, be an embedded value in said reading apparatus, e.g., a value or coefficient programmed into the instrument software algorithm, an embedded value on said assay cartridge and automatically read by said reading apparatus, e.g., a barcode, 2D barcode, magnetic strip, a visible value, e.g., printed number or letter code, on said assay cartridge and manually entered into said reading apparatus, or a visible value, e.g., printed number or letter code, on said assay cartridge package and manually entered into said reading apparatus.

In one embodiment of the invention, a dry reagent, e.g., ferrocene monocarboxylic acid, is added to the portion of the sample dilution chamber and parameters are set to give a known dissolved concentration of ferrocene in the blood sample, e.g., 0.1 to 10 mM or about 1.0 mM. In certain embodiments, one or more sensors in the cartridge can be used to detect the ferrocene signal for the diluted sample during the sandwich formation step. For an intended hundred fold dilution, for example, the signal may be equivalent to 10 $\mu$M ferrocene. During factory calibration, a current versus concentration algorithm can be established and embedded in the instrument software. Without being bound by theory, as ferrocene gives an outer sphere electron transfer reaction, the signal should not depend on the electrode catalytic activity. Ferrocene monocarboxylic acid has a half-wave potential about 200 mV more positive than the p-aminophenol (PAP) used to detect the sandwich, so it should not provide a material signal, even if the wash step leaves residue.

In another embodiment, the sample is introduced to the device and passes onto the sample isolation unit or, in other embodiments of the invention, to the fixed sample extraction unit. When the dilution elements are actuated and the diluted sample is passed to the detection region of the immunosensing device, in certain embodiments of the invention, a portion of the diluted sample may be manually removed and tested using a potentiometric sensor or other electrochemical analysis system for amperometric measurements, a potentiometer for potentiometric electrochemical tests, or a spectrophotometer to determine the dilution determinant marker concentration. The ratio of the dilution determinant marker concentration in the undiluted sample to the dilution determinant marker concentration in the analyzed portion of the diluted sample provides the dilution ratio for any given design, and by repeating the characterization for a set of devices, the precision and accuracy of the dilution process may be calculated. As such, embodiments of the present invention provide for independent empirical verification of accuracy and precision of dilution system designs. Use of the dilution determinant marker may also serve as a control test during actual use of the immunosensing device of the present invention.

While an assay may, in principle, require a defined target dilution ratio (e.g., 5,000:1), in some embodiments of the present invention, it may be found that a particular sample isolation unit or fixed sample extraction unit dilution has high precision but is inaccurate (e.g., gives a ratio of 5,300:1). In certain embodiments, the assay coefficients are adjusted (in this example, to a 5,300:1 ratio) rather than reengineer the design elements. Those skilled in the art will recognize that for practical assay development using a single-use cartridge format, this is one viable approach. Note that while the present disclosure uses integer ratios for convenience, fractional ratios, e.g., 2:7, 2:7.1, 2:7.01, may also be within the scope of the invention.

In preferred embodiments of the invention, the diluent fluid is a stimulant of plasma without the presence of the analyte. In certain embodiments, the diluent fluid is aqueous based and includes electrolytes, buffers and proteins typically found in plasma at high concentration, e.g., albumin and immunoglobulins. The diluent fluid may also include lysing agents, stabilizers, and antibacterial agents, which are well-known in the clinical biochemical arts.

With regard to the transit time of the diluent fluid in contact with the controlled dilution device (e.g., time during washing or the extraction of a portion of the analyte out of the controlled dilution device), the diluent fluid volume will generally be selected in the range of about 5 $\mu$L to about 200 $\mu$L. In some embodiments, the transit time across the surface (e.g., face or edge) of the controlled dilution device may be in the range of about 0.1 second to about 100 seconds (e.g., 1 second to 50 seconds or 2 seconds to 10 seconds).

In certain embodiments, the diluent fluid is transported through the conduit and across the surface of the controlled dilution device at a substantially fixed flow rate, e.g. 10 $\mu$L/s. The quicker the diluent fluid moves, the less time is provided for extraction of analyte from the dilution device. As such, rate of fluid flow is a control parameter for the assay system. In some embodiments, the fluid flow can be controlled by an instrument mechanism and software, which control actuation of the pump elements. Alternative embodiments to control of flow rate include a pump cycle that has a fixed stationary dwell time for a portion of the diluent fluid in contact with the surface of the controlled dilution device, and also a pump cycle that oscillates a portion of the diluent across the surface of the controlled dilution device. In these embodiments, one or more software programs can be utilized to control the instrument mechanism interaction with the pump elements.

With regard to the fixed sample extraction unit for high levels of dilution, in some embodiments, instrument software includes a delay feature such that the instrument does not deploy the diluent until sufficient time has elapsed. In a preferred embodiment, the instrument includes a detector switch that registers the time of insertion to the test device, and this acts as the t=0 point for the test cycle. Thus, if the fixed sample extraction unit filling step takes 15 seconds from the time the sample enters the device, diluent activation is set to be initiated at t>15 (e.g., t=20 seconds, t=30 seconds or t=60 seconds).

II. Methods of Performing Assays

The present invention is applicable to methods of performing assays with a sensor cartridge incorporating an integrated sample dilution feature and sample metering device. The methods of the invention are applicable to various biological sample types (e.g., blood, plasma, serum, urine, interstitial fluid and cerebrospinal fluid).

In some embodiments, the sensor cartridge is an ion sensor (e.g., potentiometric sensor for K, Na, Cl, Ca, $NH_4$ and the like); a metabolite sensor (e.g., amperometic enzymatic sensor for glucose, creatinine, cholesterol and the like); an enzyme activity sensor (e.g., for liver tests including ALT and AST); and a nucleotide sensor (e.g., where amplified target ssDNA forms a sandwich with ssDNA immobilized on the sensor and other complimentary ssDNA labeled with a signal moiety such as an enzyme or fluorescent species).

In preferred embodiments, the present invention may be employed in one or more of the following areas: immunosensors, most notably in the context of point-of-care testing; electrochemical immunoassays; immunosensors in conjunction with immuno-reference sensors; whole blood immunoassays; single-use cartridge based immunoassays; and non-sequential immunoassays with only a single wash step; and dry reagent coatings. As will be appreciated by those skilled in the art, the general concept disclosed herein is applicable to many immunoassay methods and platforms. In addition, the present invention is applicable a variety of immunoassays, including both sandwich and competitive immunoassays.

After controlled sample dilution and sandwich formation on an immunosensor, in accordance with various embodiments of the invention, wash or diluent is deployed. The diluent is preferably advanced through the connecting conduit and across the sensors by a sequence of small displacement steps formed by alternating air and fluid segments. In some embodiments, segment formation is achieved by the instrument applying a displacement force to actuators in contact with the air bladder and diluent package in an alternating sequence. This process effectively entrains a set of air and fluid segments over the sensor. It has been found that the meniscus between each segment is the most effective part of the wash cycle to remove sample, unbound analyte and unbound signal antibody from the sandwich formation or sensor region of the cartridge. In addition, a sequence of segments provides a more complete wash of the sensor compared to the same volume of diluent applied in a single pass over the sensor, although the latter may be used in assays where non-specific binding is not a significant issue. In preferred embodiments, the air and fluid segments each have a volume of about 2 µL, but the segment volume can range from less than 1 µL to more than 20 µL. In certain embodiments of the invention where the analysis conduit has a cross-sectional area of about 1-2 $mm^3$, each fluid segment is separated by an air gap of about 2-3 mm. In addition, in some embodiments, a conductivity sensor may be positioned in the analysis conduit to monitor the position of fluid-air interfaces and provide feedback control to the instrument software for pump actuation. (See, for example, the materials described in jointly-owned U.S. Pat. No. 7,419,821, which is referenced above and hereby incorporated by reference in its entirety.)

In alternative embodiments, a segment is injected using a passive feature. A well in the base of the cartridge is sealed by a tape gasket. The tape gasket covering the well has two small holes on either end. One hole is open while the other is covered with a filter material that wets upon contact with a fluid. The well is filled with a loose hydrophilic material such as, for example, a cellulose fiber, paper or glass fiber. The hydrophilic material draws the liquid into the well in the base via capillary action, displacing the air that was formerly in the well. The air is expelled through the opening in the tape gasket, creating a segment whose volume is determined by the volume of the well and the volume of the loose hydrophilic material. The material used to cover one of the inlets to the well in the base can be chosen to meter the rate at which the fluid fills the well and thereby control the rate at which the segment is injected into the conduit in the cover. This passive feature permits any number of controlled segments to be injected at specific locations within a fluid path and requires a minimum of space.

Within a segment of sample or fluid, an amending substance can be preferentially dissolved and concentrated within a predetermined region of the segment. This is achieved through control of the position and movement of the segment. Thus, for example, if only a portion of a segment, such as the leading edge, is reciprocated over the amended substance, then a high local concentration of the substance can be achieved close to the leading edge. Alternatively, if an homogenous distribution of the substance is desired, for example if a known concentration of an amending substance is required for a quantitative analysis, then further reciprocation of the sample or fluid will result in mixing and an even distribution.

In various embodiments of the invention, one or more portions of the components, conduits, and/or controlled dilution device can be coated with a dry reagent to amend a sample or fluid. The sample or fluid is passed at least once over the dry reagent coating to dissolve it. Reagents used to amend samples or fluid within the cartridge include, but are not limited to antibody-enzyme conjugates, signal antibodies to the target analyte, or blocking agents that prevent either specific or non-specific binding reactions among assay compounds. A surface coating that is not soluble, but helps prevent non-specific adsorption of assay components to the inner surfaces of the cartridges can also be utilized in some embodiments of the present invention.

As described above, the immunosensor cartridge may further include an individual diluent package containing a diluent and/or an individual reagent fluid package containing a reagent fluid. In certain embodiments, these packages are in the form of a rupturable pouch (e.g., foil pouch). Manufacture of the rupturable pouches may be performed, for example, as described in jointly-owned U.S. Pat. Appln. Pub. No. 2010/0068097 A1 to Ade et al. or in jointly-owned U.S. Pat. No. 5,096,669 to Lauks et al., the entirety of each of which is incorporated herein by reference.

The composition of the diluent is preferably selected to include a buffer, pH, detergents and the like to promote removal of the unbound sample and non-specifically bound signal antibody, without substantial effect on the stability of the sandwich formed on the immunosensor. Those skilled in the immunoassay art will recognize that such diluent compositions are well-known, as are methods for their optimization for a given assay format. In some embodiments of the invention, the volume of the diluent in the diluent package is selected to be in the range of about 50 to about 200 µL.

The composition of the detection or reagent fluid is selected to include an enzyme substrate, buffer, pH, detergents and the like to promote efficient activity of the enzyme on the signal antibody, without substantial effect on the stability of the sandwich formed on the immunosensor. Reagent fluid compositions are well-known in the immunoassay art, as are methods for their optimization for a given assay format. In some embodiments, the detection fluid in the detection fluid package is in the volume range of about 50 µL to about 200 µL and contains p-aminophenol (PAP) phosphate as a substrate for the alkaline phosphatase enzyme label in a buffered solution at pH 9.8.

III. Ratiometric Immunoassays

Given the relative sensitivity of the antibodies that are used and the actual whole blood concentrations of certain protein molecules (e.g., hemoglobin or albumin), it may be desirable to reduce their respective concentrations, for example, down to the range of about 1 to 100 ng/mL, which is roughly a 500 to 5000 fold dilution. In these embodiments, accurate dilution is not critical. Rather, the sample need only be diluted down to the analyte concentration range where the sensor response is quasi-linear.

In certain embodiments, the sample isolation unit approach for low-range dilutions can be utilized to perform a ratiometric assay in a blood sample. For example, in one embodiment of the present invention, a method of performing a ratiometric assay in a blood sample is provided comprising introducing a blood sample into a sample dilution chamber of a cartridge, wherein the dilution chamber is located between a diluent introduction port and a sample isolation unit, and wherein the volume between the diluent introduction port and the sample isolation unit defines a metered volume of said sample for dilution. The metered volume of the sample is diluted with a metered volume of diluent (as described above) from a diluent conduit located within the cartridge to form a diluted sample. The diluted sample is pumped to a first and second sensor in a sensing region (e.g., analysis conduit) of the cartridge, the first sensor comprising an immunosensor for a first analyte and the second sensor comprising an immunosensor for a second analyte. A first sandwich is formed on the first sensor comprising an immobilized first analyte antibody, the first analyte and a first analyte antibody labeled with a signaling moiety, and a second sandwich is formed on the second sensor comprising an immobilized second analyte antibody, the second analyte and a second analyte antibody labeled with the signaling moiety. The diluted sample is subsequently washed from the sensing region of the cartridge, optionally with a wash fluid that is the same composition as the diluent, and a reagent is introduced for generating a signal from the signaling moiety to the sensing region of the cartridge. The signal at said first and second sensors is detected and recorded, and the fractional percentage of the first analyte to the second analyte is determined from the signal at said first and second sensors.

In certain embodiments, the sample isolation unit approach for high-range dilutions can be utilized to perform a ratiometric assay in a blood sample. For example, in one embodiment, the invention is to a method of performing a ratiometric assay in a blood sample, comprising introducing a blood sample into a sample introduction chamber of a cartridge, wherein the introduction chamber terminates in a fixed sample extraction unit, and wherein a distal portion of said extraction unit defines a metered volume of a sample for dilution. The metered volume of the sample is diluted with a metered volume of diluent from a diluent conduit located within the cartridge to form a diluted sample, which is pumped to first and second sensors in a sensing region of the cartridge. The first sensor comprises an immunosensor for a first analyte and the second sensor comprises an immunosensor for a second analyte. A first sandwich is formed on the first sensor comprising an immobilized first analyte antibody, the first analyte and a first analyte antibody labeled with a signaling moiety, and a second sandwich is formed on the second sensor comprising an immobilized second analyte antibody, the second analyte and a second analyte antibody labeled with the signaling moiety. The diluted sample is subsequently washed from the sensing region of the cartridge, and a reagent for generating a signal from the signaling moiety is introduced to the sensing region of the cartridge. The signal at said first and second sensors is detected and recorded and the fractional percentage of the first analyte to the second analyte is determined from the signal at said first and second sensors.

In certain embodiments of the invention, the first analyte comprises hemoglobin and the second analyte comprises hemoglobin A1c. In this embodiment, the dilution chamber or the controlled dilution device preferably comprises a lysing agent (e.g., sodium deoxycholate or saponin) capable of dissolving in the sample, the diluent or the diluted sample. In other embodiments where the first analyte comprises albumin and the second analyte comprises glycosylated albumin, a lysing agent is not required.

EXAMPLES

The present invention will be better understood with reference to the specific embodiments set forth in the following non-limiting prophetic examples. Suitable non-limiting examples of analytes detectable with the low dilution format are hemoglobin A1c and C-reactive protein. Suitable non-limiting examples of analytes detectable with high dilution format are hemoglobin, human serum albumin and immunoglobulins, e.g., IgG and IgA. Typical disease states include anemia and immunity assessment. In addition, detection of beta human chorionic gonadotropin (bHCG) can be extended into the range of about 50,000 to 500,000 ng/mL.

Example 1

Amperometric Immunoassay

Figure 11:
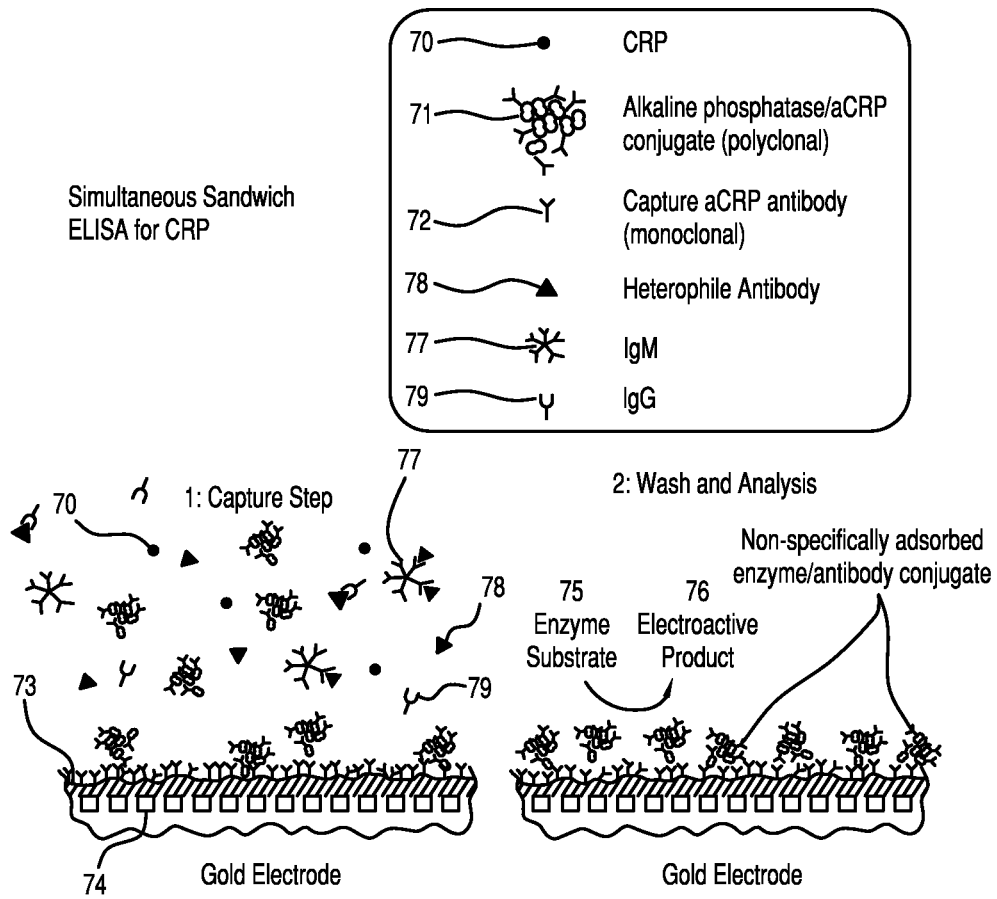
FIG. 11 illustrates the principle of operation of an electrochemical immunosensor.

FIG. 11 illustrates the principle of an amperometric immunoassay according to specific non-limiting embodiments of the present invention for determination of C-reactive protein (CRP) 70 in a diluted fluid sample, a marker of inflammation. A diluted sample (e.g., whole blood sample) according to the invention, as described above (either high or low range dilution, but preferably the latter for CRP) is mixed with a conjugate molecule 71 comprising alkaline phosphatase enzyme (AP) covalently attached to a polyclonal anti-CRP antibody (aCRP) 72. The conjugate 71 specifically binds to CRP 70 in the sample, producing a complex made up of CRP 70 bound to the AP-aCRP conjugate 71. In a capture step, this complex binds to the capture aCRP antibody 72 attached onto the surface of or unattached but proximate to the sensor (e.g., gold electrode 74). In some embodiments, a conductivity sensor (not shown) is used to monitor when a certain volume of the sample (e.g., sample segment) reaches the sensor. The time of arrival of the sample can be used to detect leaks within the cartridge (e.g., a delay in arrival signals a leak). The position of the sample segment within the analysis conduit can be actively controlled using the edge of the fluid sample as a marker. As the sample/air interface crosses the conductivity sensor, a precise signal is generated that can be used as a fluid marker from which controlled fluid excursions can be executed. The sample segment is preferentially oscillated edge-to-edge over the sensor 74 in order to present the entire sample to the sensor surface. A second reagent can be introduced in the analysis conduit beyond the sensor, which becomes homogenously distributed during the fluid oscillations. The sensor chip contains a capture region or regions coated with antibodies for the analyte of interest. These capture regions are defined by a hydrophobic ring of polyimide or another photolithographically produced layer. A microdroplet or several microdroplets (5-40 nL in size) containing antibodies in some form, e.g., bound to latex microspheres, is dispensed on the surface of the sensor. The photodefined ring contains the one or more aqueous droplets, allowing the antibody coated region to be localized to a precision of a few microns. In some embodiments, the capture region can be made from 0.03 $mm^2$ to 2 $mm^2$ in size. The upper end of this size range is limited by the size of the conduit and sensor in certain embodiments, and is not a limitation of the invention.

Thus, the gold electrode 74 is coated with a biolayer 73 comprising a covalently attached anti-CRP antibody, to which the CRP/AP-aCRP complex binds. AP is thereby immobilized close to the electrode in proportion to the amount of CRP initially present in the sample. In addition to specific binding, the enzyme-antibody conjugate may bind non-specifically to the sensor. Non-specific binding provides a background signal from the sensor that is undesirable and preferably is minimized. As described above, the rinsing protocols, and in particular the use of segmented fluid to rinse the sensor, provide efficient means to minimize this background signal. In a second step subsequent to the rinsing step, a substrate 75 that is hydrolyzed by, for example, alkaline phosphatase to produce an electroactive product 76 is presented to the sensor. The amperometric electrode is either clamped at a fixed electrochemical potential sufficient to oxidize or reduce a product of the hydrolyzed substrate but not the substrate directly, or the potential is swept one or more times through an appropriate range. Optionally, a second electrode may be coated with a layer where the complex of CRP/AP-CRP is made during manufacture, to act as a reference sensor or calibration means for the measurement.

In the present example, the sensor comprises two amperometric electrodes that are used to detect the enzymatically produced 4-aminophenol from the reaction of 4-aminophenylphosphate with the enzyme label alkaline phosphatase. The electrodes are preferably produced from gold surfaces coated with a photodefined layer of polyimide. Regularly spaced openings in the insulating polyimide layer define a grid of small gold electrodes at which the 4-aminophenol is oxidized in a 2 electron per molecule reaction.

$$H_2N-C_6H_4-OH \rightarrow HN=C_6H_4=O+2H^++2e^-$$

Sensor electrodes further comprise a biolayer, while reference electrodes can be constructed, for example, from gold electrodes lacking a biolayer, or from silver electrodes, or other suitable material. Different biolayers can provide each electrode with the ability to sense a different analyte.

Substrates, such as p-aminophenol (PAP) species, can be chosen such that the $E_{1/2}$ of the substrate and product differ substantially. Preferably, the $E_{1/2}$ of the substrate is substantially higher than that of the product. When the condition is met, the product can be selectively electrochemically measured in the presence of the substrate. In specific embodiments, the substrate is comprised of a phosphorylated ferrocene or, more preferably, phosphorylated PAP.

The size and spacing of the electrode play an important role in determining the sensitivity and background signal. The important parameters in the grid are the percentage of exposed metal and the spacing between the active electrodes. The position of the electrode can be directly underneath the antibody capture region or offset from the capture region by a controlled distance. The actual amperometric signal of the electrodes depends on the positioning of the sensors relative to the antibody capture site and the motion of the fluid during the analysis. A current at the electrode is recorded that depends upon the amount of electroactive product in the vicinity of the sensor.

The detection of alkaline phosphatase activity in this example relies on a measurement of the 4-aminophenol oxidation current. This is achieved at a potential of about +60 mV versus the Ag/AgCl ground chip. The exact form of detection used depends on the sensor configuration. In one version of the sensor, the array of gold microelectrodes is located directly beneath the antibody capture region. When the diluent is pulled over this sensor, enzyme located on the capture site converts the 4-aminophenylphosphate to 4-aminophenol in an enzyme limited reaction. The concentration of the 4-aminophenylphosphate is selected to be in excess, e.g., 10 times the Km value. The analysis solution is 0.1 M in diethanolamine, 1.0 M NaCl, buffered to a pH of 9.8. Additionally, the analysis solution contains 0.5 mM MgCl, which is a cofactor for the enzyme.

In another electrode geometry embodiment, the electrode is located a few hundred microns away from the capture region. When a fresh segment of diluent is pulled over the capture region, the enzyme product builds with no loss due to electrode reactions. After a time, the solution is slowly pulled from the capture region over the detector electrode, resulting in a current spike from which the enzyme activity can be determined.

An important consideration in the sensitive detection of alkaline phosphatase activity is the non-4-aminophenol current associated with background oxidations and reductions occurring at the gold sensor. Gold sensors tend to give significant oxidation currents in basic buffers at these potentials. The background current is largely dependent on the buffer concentration, the area of the gold electrode (exposed area), surface pretreatments and the nature of the buffer used. Diethanolamine is a particularly good activating buffer for alkaline phosphatase. At molar concentrations, the enzymatic rate is increased by about three times over a non-activating buffer such as carbonate.

In alternative embodiments, the enzyme conjugated to an antibody or other analyte-binding molecule is urease, and the substrate is urea. Ammonium ions produced by the hydrolysis of urea are detected in this embodiment by the use of an ammonium sensitive electrode. Ammonium-specific electrodes are well-known to those of skill in the art. A suitable microfabricated ammonium ion-selective electrode is disclosed in U.S. Pat. No. 5,200,051, which is referenced above and hereby incorporated by reference in its entirety. Other enzymes that react with a substrate to produce an ion are known in the art, as are other ion sensors for use therewith. For example, phosphate produced from an alkaline phosphatase substrate can be detected at a phosphate ion-selective electrode.

Figure 12:
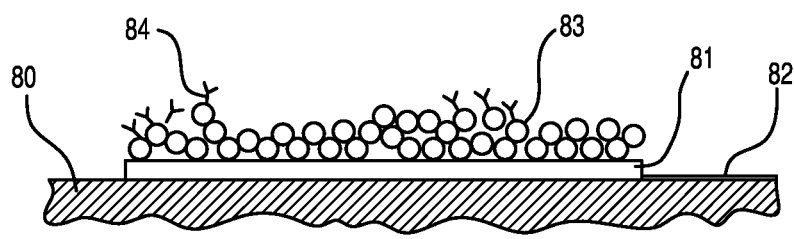
FIG. 12 a side view of the construction of an electrochemical immunosensor with antibody-labeled particles (not drawn to scale)

Referring now to FIG. 12, there is illustrated the construction of an embodiment of a microfabricated immunosensor. Preferably, a planar non-conducting substrate is provided 80, onto which is deposited a conducting layer 81 by conventional means or microfabrication, known to those of skill in the art. The conducting material is preferably a noble metal such as gold or platinum, although other unreactive metals such as iridium may also be used, as may non-metallic electrodes of graphite, conductive polymer, or other materials. An electrical connection 82 is also provided. A biolayer 83 is deposited onto at least a portion of the electrode. In the present disclosure, a biolayer refers to a porous layer comprising on its surface a sufficient amount of a molecule 84 that can either bind to an analyte of interest, or respond to the presence of such analyte by producing a change that is capable of measurement. Optionally, a permselective screening layer may be interposed between the electrode and the biolayer to screen electrochemical interferents as described in U.S. Pat. No. 5,200,051, which is referenced above and hereby incorporated by reference in its entirety.

In some embodiments of the present invention, a biolayer is constructed from latex beads of specific diameter in the range of 0.001 μm to 50 μm. The beads are modified by covalent attachment of any suitable molecule consistent with the above definition of a biolayer. Many methods of attachment exist in the art, including providing amine reactive N-hydroxysuccinimide ester groups for the facile coupling of lysine or N-terminal amine groups of proteins. In specific embodiments, the biomolecule is chosen from among ionophores, cofactors, polypeptides, proteins, glycopeptides, enzymes, immunoglobulins, antibodies, antigens, lectins, neurochemical receptors, oligonucleotides, polynucleotides, DNA, RNA, or suitable mixtures. In more specific embodiments, the biomolecule is an antibody selected to bind one or more of human chorionic gonadotrophin, C-reactive protein, hemoglobin, hemoglobin A1c, IgG, IgA, brain natriuretic peptide (BNP), troponin I, troponin T, troponin C, a troponin complex, creatine kinase, creatine kinase subunit M, creatine kinase subunit B, myoglobin, myosin light chain, or modified fragments of these. Such modified fragments are generated by oxidation, reduction, deletion, addition or modification of at least one amino acid, including chemical modification with a natural moiety or with a synthetic moiety. Preferably, the biomolecule binds to the analyte specifically and has an affinity constant for binding analyte ligand of about $10^7$ to $10^{15}$ $M^{-1}$.

In one embodiment, the biolayer, comprising beads having surfaces that are covalently modified by a suitable molecule, is affixed to the sensor by the following method. A microdispensing needle is used to deposit onto the sensor surface a small droplet, preferably about 0.4 nL, of a suspension of modified beads. The droplet is permitted to dry, which results in a coating of the beads on the surface that resists displacement during use.

In addition to immunosensors in which the biolayer is in a fixed position relative to an amperometric sensor, the present invention also envisages embodiments in which the biolayer is coated upon particles that are mobile. In certain embodiments, the cartridge can contain mobile microparticles capable of interacting with an analyte, for example magnetic particles that are localized to an amperometric electrode subsequent to a capture step, whereby magnetic forces are used to concentrate the particles at the electrode for measurement. See, for example, jointly-owned U.S. patent application Ser. No. 12/815,132 and U.S. Provisional Pat. Appln. Ser. Nos. 61/371,066; 61/371,109; 61/371,077; and 61/371,085. Each of these patent applications is hereby incorporated by reference in its entirety. One advantage of mobile microparticles in the present invention is that their motion in the sample or fluid accelerates binding reactions, making the capture step of the assay faster. For certain embodiments using non-magnetic mobile microparticles, a porous filter is used to trap the beads at the electrode.

Figure 13:
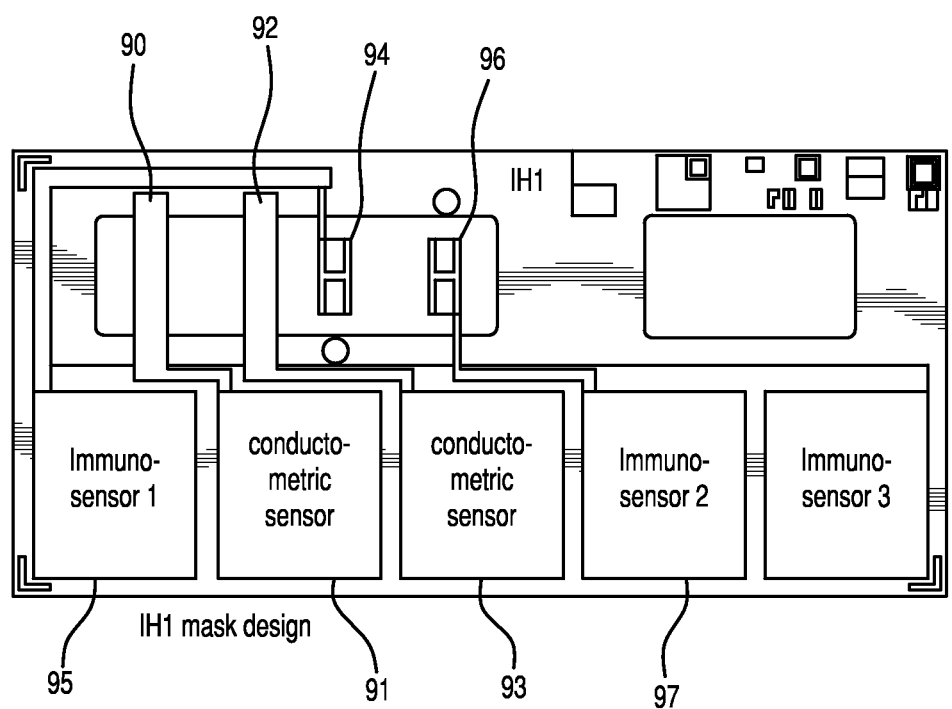
FIG. 13 is a top view of the mask design for the conductimetric and immunosensor electrodes for an immunosensor cartridge in accordance with one embodiment of the present invention.

Referring now to FIG. 13, there is illustrated a mask design for several electrodes upon a single substrate in accordance with one embodiment of the present invention. By masking and etching techniques, independent electrodes and leads can be deposited. Thus, a plurality of immunosensors, 94 and 96, and conductimetric sensors, 90 and 92, are provided in a compact area at low cost, together with their respective connecting pads, 91, 93, 95, and 97, for effecting electrical connection to the reading apparatus. In principle, a very large array of sensors can be assembled in this way, each sensitive to a different analyte or acting as a control sensor.

In specific embodiments of the present invention, immunosensors are prepared as follows. Silicon wafers are thermally oxidized to form an insulating oxide layer having a thickness of about 1 μm. A titanium/tungsten layer is sputtered onto the oxide layer to a preferable thickness of between 100-1000 Å, followed by a layer of gold that is most preferably 800 Å thick. Next, a photoresist is spun onto the wafer and is dried and baked appropriately. The surface is then exposed using a contact mask, such as a mask corresponding to that illustrated in FIG. 13. The latent image is developed, and the wafer is exposed to a gold-etchant. The patterned gold layer is coated with a photodefinable polyimide, suitably baked, exposed using a contact mask, developed, cleaned in an $O_2$ plasma, and preferably imidized at 350° C. for about 5 hours. The surface is then printed with antibody-coated particles. Droplets, preferably of about 0.4 nL volume and containing 2% solid content in deionized water, are deposited onto the sensor region and are dried in place by air drying. Optionally, an antibody stabilization reagent (e.g., StabilCoat® SurModics, Inc., Eden Prairie, Minn., USA) is overcoated onto the sensor. Drying the particles causes them to adhere to the surface in a manner that prevents dissolution in either sample or fluid containing a substrate. This method provides a reliable and reproducible immobilization process suitable for manufacturing sensor chips in high volume.

Example 2

Immunosensing Device and Method of Use

The present example describes one of the methods of use of a cartridge embodied in the present invention. In this embodiment, the cartridge includes a closeable valve, located between the immunosensor and the waste chamber. For a CRP assay, a blood sample is first introduced into the sample chamber of the cartridge. In the following time sequence, time zero (t=0) represents the time at which the cartridge is inserted into the cartridge reading device. Times are given in minutes. Between t=0 and t=1.5, the cartridge reading device makes electrical contact with the sensors through electrical contact pads and performs certain diagnostic tests. Insertion of the cartridge perforates the foil pouch introducing diluent into the wash conduit, as previously described, as well as into the diluent conduit. The diagnostic tests determine whether fluid or sample is present in the conduits using the conductivity electrodes, determine whether electrical short circuits are present in the electrodes, and ensure that the sensor and ground (e.g., reference/counter) electrodes are thermally equilibrated to, preferably, 37° C. prior to the analyte determination.

Between t=0.5 and t=1.5, the pumping means pumps a metered diluent from the diluent conduit into a dilution chamber, where the diluent is mixed with a metered portion of the sample to form a diluted sample.

Between t=1.5 and t=6.75, the diluted sample, preferably between about 4 μL and about 200 μL, more preferably between about 4 μL and about 20 μL, and most preferably about 7 μL, is used to contact the sensor. The edges defining the forward and trailing edges of the diluted sample are reciprocally moved over the conductivity sensor region at a frequency that is preferably between 0.2 to 5.0 Hz, and is most preferably 0.7 Hz. During this time, the enzyme-antibody conjugate and beads (e.g., mobile beads or magnetically-susceptible beads) dissolve within the sample. The amount of enzyme-antibody conjugate that is coated onto the conduit is selected to yield a concentration when dissolved that is preferably higher than the highest anticipated CRP concentration, and is most preferably six times higher than the highest anticipated CRP concentration in the sample.

Between t=6.75 and t=10.0, the diluted sample is moved to the immunosensor for capture of the beads. As shown in FIGS. 1-4, the sample is moved into the waste chamber via closeable valve 41, wetting the closeable valve and causing it to close. The seal created by the closing of the valve 41 permits the first pump means to be used to control motion of fluid from conduit 11 to analysis conduit 15. After the valve 41 closes and the remaining sample is locked in the post analysis conduit, the analyzer plunger retracts from the flexible diaphragm of the pump means, creating a partial vacuum in the analysis conduit. This forces the diluent through the small hole in the tape gasket 21 and into a short transecting conduit 8 in the base, and then up through another hole in gasket 21 and into analysis conduit 15 (in cover 1). The diluent is then pulled further and the front edge of the diluent (acting here as wash fluid) is oscillated across the surface of the immunosensor chip in order to shear the sample near the walls of the conduit. The conductivity sensor on the chip is used to control this process.

The efficiency of the wash is optimally further enhanced by introduction into the fluid of one or more menisci or air segments. The air segments may be introduced by either active or passive means. Fluid is then forcibly moved towards the sensor chip by the partial vacuum generated by reducing the mechanical pressure exerted upon pump membrane 9, causing the analysis conduit 15 in the vicinity of transecting conduit 8 to fill with diluent as wash fluid. This region of the analysis conduit optionally has a higher channel height resulting in a meniscus with a smaller radius of curvature. The region of the analysis conduit in the direction of the one or more sensors optionally has a conduit height is that is smaller. In one aspect, the diluent passively flows from the region adjacent the transecting conduit 8 towards this low height region of the analysis conduit, thereby washing the conduit walls. This passive wicking effect allows further effective washing of the analysis conduit using a minimal volume of fluid and without displacing the beads that are attached to the sensor. In this embodiment, the fluid located within the wash conduit may also contain a substrate for the enzyme. In other embodiments, amendment of the fluid using dried substrate within the wash conduit may be utilized.

Following the positioning of a final segment of fluid over the sensor, measurement of the sensor response is recorded and the concentration of analyte is determined. Specifically, at least one sensor reading of a sample is made by rapidly placing over the sensor a fresh portion of fluid containing a substrate for the enzyme. Rapid displacement both rinses away product previously formed, and provides a new substrate to the electrode. Repetitive signals are averaged to produce a measurement of higher precision, and also to obtain a better statistical average of the baseline, represented by the current immediately following replacement of the solution over the immunosensor.

The invention described and disclosed herein has numerous benefits and advantages compared to previous devices. These benefits and advantages include, but are not limited to ease of use, the automation of most if not all steps of the analysis, which eliminates user included error in the analysis. While the invention has been described in terms of various preferred embodiments, those skilled in the art will recognize that various modifications, substitutions, omissions and changes can be made without departing from the spirit of the present invention. Accordingly, it is intended that the scope of the present invention be limited solely by the scope of the following claims.

What is claimed is:

1. A sensor cartridge for sensing at least one analyte in a sample, comprising:
    at least one sensor in an analysis conduit;
    a sample chamber between a sample entry port and a sample extraction unit;
    a diluent package containing a diluent;
    a diluent conduit configured for transporting diluent from the diluent package directly to the sample extraction unit; and
    a pump configured to transfer said diluent through said diluent conduit, over and/or through said sample extraction unit, and into said analysis conduit.

2. The sensor cartridge of claim 1, wherein a distal portion of said extraction unit defines a metered volume of said sample.

3. The sensor cartridge of claim 1, wherein said extraction unit comprises a porous hydrophilic material.

4. The sensor cartridge of claim 1, wherein said extraction unit comprises a cellulose material.

5. The sensor cartridge of claim 1, wherein said extraction unit comprises nitrocellulose.

6. The sensor cartridge of claim 1, wherein said extraction unit comprises cotton fiber.

7. The sensor cartridge of claim 1, wherein said extraction unit comprises paper.

8. The sensor cartridge of claim 1, wherein said extraction unit comprises glass-filled paper.

9. The sensor cartridge of claim 1, wherein said extraction unit comprises a transverse filter material.

10. The sensor cartridge of claim 1, wherein said extraction unit comprises a porous outer coating.

11. The sensor cartridge of claim 1, wherein said extraction unit comprises a lysing agent.

12. The sensor cartridge of claim 11, wherein said lysing agent comprises sodium deoxycholate.

13. The sensor cartridge of claim 11, wherein said lysing agent comprises saponin.

14. The sensor cartridge of claim 1, wherein said diluent conduit defines a metered volume of diluent.

15. The sensor cartridge of claim 1, wherein said cartridge has opposing surfaces that are folded together.

16. The sensor cartridge of claim 1, wherein said cartridge is a single-use cartridge.

17. The sensor cartridge of claim 1, wherein said sensor is an immunosensor.

18. The sensor cartridge of claim 1, wherein said sensor is selected from the group consisting of an ion sensor, a metabolite sensor, an enzymatic sensor, an enzyme activity sensor and a nucleotide sensor.

19. The sensor cartridge of claim 1, wherein said cartridge is configured to dilute said sample at a dilution ratio of about 50:1 to about 50,000:1 (v/v diluent:sample).

* * * * *